(12) United States Patent
Domingo et al.

(10) Patent No.: US 11,672,738 B2
(45) Date of Patent: Jun. 13, 2023

(54) APPARATUS AND METHODS FOR DISPENSING ORAL TRANSMUCOSAL DOSAGE FORMS

(71) Applicant: AcelRx Pharmaceuticals, Inc., Redwood City, CA (US)

(72) Inventors: Casidy Domingo, San Mateo, CA (US); Edmond Chiu, San Francisco, CA (US); Bradley Blackwood, San Jose, CA (US)

(73) Assignee: Vertical Pharmaceuticals, LLC, Alpharetta, GA (US)

( * ) Notice: Subject to any disclaimer, the term of this patent is extended or adjusted under 35 U.S.C. 154(b) by 462 days.

(21) Appl. No.: 15/965,285

(22) Filed: Apr. 27, 2018

(65) Prior Publication Data
US 2018/0243169 A1 Aug. 30, 2018

Related U.S. Application Data

(63) Continuation of application No. PCT/US2016/059577, filed on Oct. 28, 2016.
(Continued)

(51) Int. Cl.
  *A61J 7/00* (2006.01)
  *A61M 5/315* (2006.01)
  *A61M 37/00* (2006.01)

(52) U.S. Cl.
  CPC ........... *A61J 7/0076* (2013.01); *A61J 7/0053* (2013.01); *A61J 7/0084* (2013.01); *A61M 5/315* (2013.01); *A61M 37/0069* (2013.01)

(58) Field of Classification Search
  CPC ............ A61M 31/007; A61M 37/0069; A61M 25/0023; A61M 5/31501;
(Continued)

(56) References Cited

U.S. PATENT DOCUMENTS 2,621,655 A 12/1952 Olson et al.
3,162,322 A 12/1964 Gilbertson
(Continued)

FOREIGN PATENT DOCUMENTS

CN 1886166 A 12/2006
CN 1939547 A 4/2007
(Continued)

OTHER PUBLICATIONS

AcelRx Pharmaceuticals, Inc., "AcelRx Pharmaceuticals Reports Positive Results from a Clinical Trial of Sublingual Sufentanil/Triazolam NanoTabTM Combination (ARX-03) in Treating Procedural Pain and Anxiety," Jan. 12, 2009, pp. 1-2.
(Continued)

*Primary Examiner* — Emily L Schmidt
*Assistant Examiner* — Alexandra Lalonde
(74) *Attorney, Agent, or Firm* — Nelson Mullins Riley & Scarborough LLP

(57) ABSTRACT

Single dose drug dosage form dispensing devices, and methods for operating such devices are disclosed herein. In one embodiment, an apparatus includes a housing defining an actuation pathway and a pusher. At least a portion of the pusher is disposed within the actuation pathway such that distal end portions of the pusher and the housing define a volume configured to contain a drug-containing tablet. The pusher is configured to move relative to the housing in a distal direction from a first position to a second position to expel the tablet from the volume. The distal end portion of the pusher is extended from an opening in the housing when the pusher is in its second position. The housing is configured to limit movement of the pusher relative to the housing in a proximal direction towards the first position of the pusher after the tablet is expelled.

20 Claims, 10 Drawing Sheets

Related U.S. Application Data

(60) Provisional application No. 62/248,837, filed on Oct. 30, 2015.

(58) Field of Classification Search
CPC ............ A61M 2005/005; A61M 5/502; A61M 5/315; A61D 7/00; A61K 9/0024; A61F 13/266; A61J 7/0076; A61J 7/0092; A61J 7/0053; B65D 83/00
See application file for complete search history.

(56) References Cited

U.S. PATENT DOCUMENTS

| | | | |
|---|---|---|---|
| 3,238,941 A | 3/1966 | Klein et al. | |
| 3,757,781 A | 9/1973 | Smart | |
| 3,780,735 A * | 12/1973 | Crouter ................ | A61D 7/00 604/59 |
| 3,789,845 A | 2/1974 | Long | |
| 4,060,083 A | 11/1977 | Hanson | |
| 4,154,365 A | 5/1979 | Lorca | |
| 4,237,884 A | 12/1980 | Erikson | |
| 4,465,191 A | 8/1984 | Darbo | |
| 4,474,308 A | 10/1984 | Bergeron | |
| 4,657,533 A | 4/1987 | Oscarsson | |
| 4,733,797 A | 3/1988 | Haber | |
| 4,769,011 A | 9/1988 | Swaniger | |
| 4,900,303 A | 2/1990 | Lemelson | |
| 4,950,234 A | 8/1990 | Fujioka et al. | |
| 4,995,869 A * | 2/1991 | McCarthy .......... | A61M 5/5013 604/110 |
| 5,190,185 A | 3/1993 | Blechl | |
| 5,263,596 A | 11/1993 | Williams | |
| 5,292,307 A | 3/1994 | Dolzine et al. | |
| 5,296,234 A | 3/1994 | Hadaway et al. | |
| 5,304,119 A * | 4/1994 | Balaban ............ | A61M 37/0069 604/107 |
| 5,366,112 A | 11/1994 | Hinterreiter | |
| 5,366,113 A | 11/1994 | Kim et al. | |
| 5,380,295 A * | 1/1995 | Vacca .................... | A61M 5/315 604/187 |
| 5,507,807 A | 4/1996 | Shippert | |
| 5,549,560 A | 8/1996 | Van de Wijdeven | |
| 5,584,805 A | 12/1996 | Sutton | |
| 5,646,912 A | 7/1997 | Cousin | |
| 5,827,293 A | 10/1998 | Elliott | |
| 5,860,946 A | 1/1999 | Hofstatter | |
| 5,984,888 A | 11/1999 | Nielsen et al. | |
| 6,258,056 B1 | 7/2001 | Turley et al. | |
| 6,364,158 B1 | 4/2002 | Dimoulis | |
| 6,530,896 B1 * | 3/2003 | Elliott .................... | A61D 7/00 604/60 |
| 7,044,125 B2 | 5/2006 | Vedrine et al. | |
| 7,118,550 B2 | 10/2006 | Loomis | |
| 7,172,573 B1 | 2/2007 | Lamb | |
| 7,264,139 B2 | 9/2007 | Brickwood et al. | |
| 7,540,998 B2 | 6/2009 | Terwilliger et al. | |
| 7,581,657 B2 | 9/2009 | Dickmann | |
| 7,744,558 B2 | 6/2010 | Maag | |
| 7,896,192 B2 | 3/2011 | Conley et al. | |
| 8,062,248 B2 | 11/2011 | Kindel | |
| 8,142,733 B2 | 3/2012 | Creaven | |
| 8,252,328 B2 | 8/2012 | Tzannis et al. | |
| 8,252,329 B2 | 8/2012 | Tzannis et al. | |
| 8,357,114 B2 | 1/2013 | Poutiatine et al. | |
| 8,454,552 B2 | 6/2013 | Bardy | |
| 8,499,966 B2 | 8/2013 | Palmer et al. | |
| 8,535,714 B2 | 9/2013 | Palmer et al. | |
| 8,548,623 B2 | 10/2013 | Poutiatine et al. | |
| 8,574,189 B2 | 11/2013 | Poutiatine et al. | |
| 8,753,308 B2 | 6/2014 | Palmer et al. | |
| 8,778,393 B2 | 7/2014 | Palmer et al. | |
| 8,778,394 B2 | 7/2014 | Palmer et al. | |
| 8,865,211 B2 | 10/2014 | Tzannis et al. | |
| 8,865,743 B2 | 10/2014 | Palmer | |
| 8,905,964 B2 | 12/2014 | Poutiatine et al. | |
| 8,945,592 B2 | 2/2015 | Pushpala et al. | |
| 9,066,847 B2 | 6/2015 | Poutiatine et al. | |
| 9,289,583 B2 | 3/2016 | Palmer et al. | |
| 9,320,710 B2 | 4/2016 | Palmer et al. | |
| 9,642,996 B2 | 5/2017 | Palmer et al. | |
| 9,744,129 B2 | 8/2017 | Palmer et al. | |
| 10,709,881 B2 | 7/2020 | Palmer et al. | |
| 10,896,751 B2 | 1/2021 | Poutiatine et al. | |
| 11,058,856 B2 | 7/2021 | Chiu et al. | |
| 2003/0088217 A1 | 5/2003 | Bergeron et al. | |
| 2003/0173408 A1 | 9/2003 | Mosher et al. | |
| 2003/0195459 A1 | 10/2003 | Shippert | |
| 2003/0225367 A1 | 12/2003 | Sabra | |
| 2004/0025871 A1 | 2/2004 | Davies | |
| 2004/0111053 A1 | 6/2004 | Nicolette | |
| 2004/0253307 A1 | 12/2004 | Hague et al. | |
| 2005/0131386 A1 | 6/2005 | Freeman et al. | |
| 2005/0150488 A1 | 7/2005 | Dave | |
| 2005/0203542 A1 * | 9/2005 | Weber ................... | A61F 9/0017 606/107 |
| 2006/0229570 A1 | 10/2006 | Lovell et al. | |
| 2006/0259188 A1 | 11/2006 | Berg | |
| 2007/0005005 A1 | 1/2007 | Wang | |
| 2007/0260491 A1 | 11/2007 | Palmer et al. | |
| 2007/0299687 A1 | 12/2007 | Palmer et al. | |
| 2009/0010992 A1 | 1/2009 | Palmer et al. | |
| 2009/0048237 A1 | 2/2009 | Palmer et al. | |
| 2010/0331874 A1 | 12/2010 | Bardy | |
| 2011/0091544 A1 | 4/2011 | Palmer | |
| 2011/0098595 A1 | 4/2011 | Hibner | |
| 2011/0208118 A1 | 8/2011 | Katz | |
| 2011/0288128 A1 | 11/2011 | Palmer et al. | |
| 2013/0090594 A1 * | 4/2013 | Palmer .................. | A61J 7/0445 604/60 |
| 2014/0171882 A1 * | 6/2014 | Hernandez Herrero ..................... | A61F 13/266 604/288 |
| 2014/0350054 A1 | 11/2014 | Palmer et al. | |
| 2014/0378948 A1 * | 12/2014 | Mellejor ................ | A61M 5/315 604/515 |
| 2015/0105719 A1 * | 4/2015 | Haindl ................ | A61B 17/3468 604/60 |
| 2016/0022919 A1 * | 1/2016 | Cammish .......... | A61M 5/31585 604/209 |
| 2016/0175533 A1 | 6/2016 | Chiu et al. | |
| 2017/0259051 A1 | 9/2017 | Palmer et al. | |
| 2019/0027241 A1 | 1/2019 | Poutiatine et al. | |

FOREIGN PATENT DOCUMENTS

| | | | |
|---|---|---|---|
| CN | 102316918 A | 1/2012 | |
| CN | 102548601 A | 7/2012 | |
| CN | 203898925 U | 10/2014 | |
| CN | 104780962 A | 7/2015 | |
| EP | 2526985 A1 | 11/2012 | |
| JP | 9-193974 A | 7/1997 | |
| JP | 2007-517636 | 7/2007 | |
| WO | WO-03101525 A1 * | 12/2003 | .......... A61M 31/007 |
| WO | WO 2008/085765 | 7/2008 | |
| WO | WO 2009/021106 | 2/2009 | |
| WO | WO 2011/047143 A1 | 4/2011 | |

OTHER PUBLICATIONS

Bredenberg, S. et al., "In vitro and in vivo evaluation of a new sublingual tablet system for rapid oromucosal absorption using fentanyl citrate as the active substance," European Journal of Pharmaceutical Sciences, 20:327-334 (2003).

Griffin, D. et al., Reg. Anesth. Pain Med., vol. 10, American Society of Regional Anesthesia Spring Meeting (2010).

Zhang, H. et al., "Oral mucosal drug delivery: clinical pharmacokinetics and therapeutic applications," Clinical Pharmacokinetics, 41(9):661-680 (2002).

International Search Report and Written Opinion for International Application No. PCT/US2010/027437, dated Jun. 21, 2010.

Office Action for U.S. Appl. No. 13/416,236, dated Feb. 4, 2013.

(56) References Cited

OTHER PUBLICATIONS

Extended European Search Report for European Application No. 17178215.4, dated Dec. 11, 2017, 8 pages.
International Search Report and Written Opinion for International Application No. PCT/US2016/059577, dated Jan. 3, 2017, 8 pages.
European Office Action for European Application No. 17178215.4, dated Jun. 18, 2019, 4 pages.
Supplementary European Search Report for European No. 16861005.3, dated Apr. 17, 2019, 5 pages.
Chinese Office Action for Chinese Application No. 201680069735.7 dated Mar. 4, 2020, 18 pages (with English translation).
Extended European Search Report for European No. 20156766.6, dated May 18, 2020, 8 pages.
European Office Action for European No. 20156766.6, dated Jun. 9, 2021, 5 pages.

* cited by examiner

APPARATUS AND METHODS FOR DISPENSING ORAL TRANSMUCOSAL DOSAGE FORMS

CROSS-REFERENCE TO RELATED APPLICATIONS

This application is a continuation of International patent application Ser. No. PCT/US2016/059577, filed on Oct. 28, 2016, entitled "Apparatus and Methods for Dispensing Oral Transmucosal Dosage Forms," which claims priority to and the benefit of U.S. provisional application Ser. No. 62/248,837, filed on Oct. 30, 2015, entitled "Apparatus and Methods for Dispensing Oral Transmucosal Dosage Forms," the disclosures of which are incorporated herein by reference in their entireties.

BACKGROUND

Apparatus and methods described herein relate generally to drug dispensing devices and delivery mechanisms for administration of small-volume drug dosage forms, and more specifically to drug dispensing devices for a single administration of a single drug-containing tablet (or a single drug dosage), for example, to the oral mucosa.

Commercially available dispensing devices for oral transmucosal delivery of medications are limited. In particular, many known commercially available dispensing devices for dispensing medication, e.g., to a patient's mouth, are for repeatable delivery of inhaled medications, rather than medications in the form of a tablet or other drug dosage form intended to be delivered to the oral mucosa for uptake by the mucosa for systemic delivery of the medication contained therein.

Additionally, drug dosage forms for oral mucosal drug delivery are typically quite small in size, and thus may be easily dislodged and/or removed from a dispensing device without such tampering being evident to an eventual operator of the dispensing device.

Known single dose dispensing devices for dispensing a tablet or other dosage form to the oral mucosa, once used to dispense the medication therein, can be reconfigured to resemble an unused device. For example, the dispensing mechanism can be returned to or close to its original pre-dispensing position, thus producing the visual effect to a would-be operator of the device that the dispensing device is unused. Due to the small size of dosage forms for oral mucosal drug delivery, if the used dispensing device were inadvertently re-used in an attempt to dispense a dosage form therefrom, the operator and/or subject intended to receive the medication may not be aware that the medication was not actually dispensed in the subsequent attempt. This is the case, for example, even if a dosage form were present, because the operator may be unable to visually confirm the presence of the dosage form and/or the subject may not be able to feel the dosage form being dispensed onto the subject's oral mucosa.

Additionally, known single dose dispensing devices may experience friction during operation of the device, thereby causing the dosage form to rotate with respect to the device and be expelled from the device at a speed different from an intended delivery speed. Such inconsistent expulsion speeds for delivery of the dosage form from the device to the subject can result in inconsistent dosing for the subject, as a dosage form that is expelled too quickly from the device can overshoot the subject's oral mucosa and instead be delivered proximate to the subject's throat where the dosage form may be swallowed instead of remaining on the oral mucosa for a sufficient time for uptake of the drug, medication or other active ingredient in the dosage form through the oral mucosa.

Accordingly, there is a need for an improved single dose dispensing device configured to deliver a drug dosage form to an oral mucosa of subject. A need also exists for a dispensing device that can be permanently deformed upon actuation of the device to deliver the dosage form therefrom. A further need exists for a dispensing device that can prevent the dispensing mechanism from be returned to a pre-dispensation position. An additional need exists for a dispensing device configured to limit rotation of the dosage form with respect to the delivery device, thereby providing for delivery of the dosage form from the device at or close to a predetermined delivery speed.

SUMMARY

Single dose drug dosage form dispensing devices, and methods for operating such devices, are disclosed herein. In one embodiment, an apparatus includes a housing defining an actuation pathway and a pusher. At least a portion of the pusher is disposed within the actuation pathway such that a distal end portion of the pusher and a distal end portion of the housing define a volume configured to contain a drug-containing tablet. The pusher is configured to move relative to the housing in a distal direction from a first position to a second position to expel the drug-containing tablet from the volume. The distal end portion of the pusher can be extended from an opening in the housing when the pusher is in its second position. The housing is configured to limit movement of the pusher relative to the housing in a proximal direction from the second position of the pusher towards the first position of the pusher after the drug-containing tablet is expelled from the volume.

DETAILED DESCRIPTION

Figure 1A:
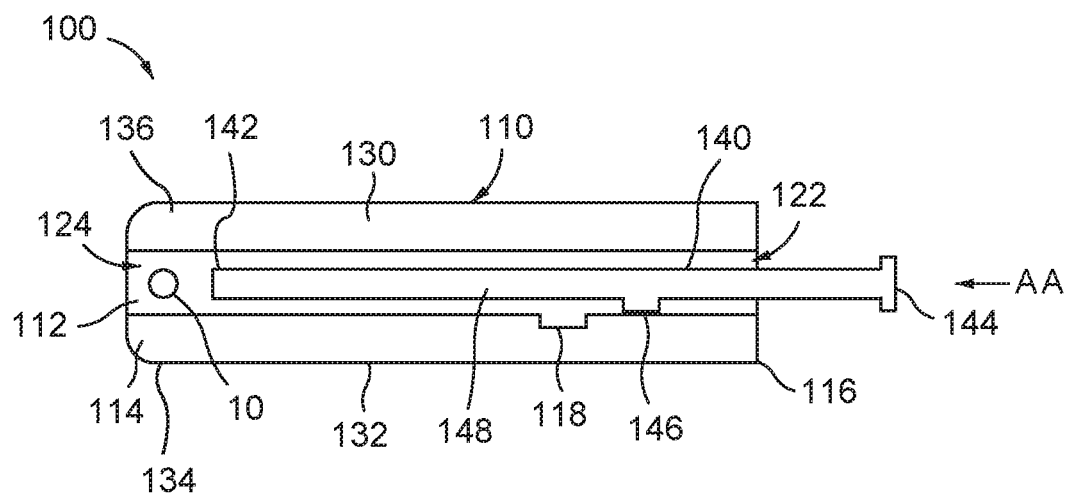
FIGS. 1A-1B are schematic illustrations of a dosage delivery device according to an embodiment, in a first configuration and a second configuration, respectively.

Drug delivery devices for administration of solid dosage forms are described herein. In some embodiments, an apparatus includes a housing and a pusher. In some embodiments, an apparatus includes a housing defining an actuation pathway and a pusher. At least a portion of the pusher is disposed within the actuation pathway such that a distal end portion of the pusher and a distal end portion of the housing define a volume configured to contain a drug-containing tablet or dosage form. The pusher is configured to move relative to the housing in a distal direction from a first position to a second position to expel the drug-containing tablet from the volume. The distal end portion of the pusher can be extended from an opening in the housing when the pusher is in its second position. The housing is configured to limit movement of the pusher relative to the housing in a proximal direction from the second position of the pusher towards the first position of the pusher after the drug-containing tablet is expelled from the volume.

In some embodiments, an apparatus includes a housing and a pusher. The housing has a first portion and a second portion and defines an actuation pathway between the first portion and the second portion. A distal end portion of the first portion of the housing is configured to deform away from a distal end portion of the second portion of the housing to produce an opening for delivery of a drug-containing tablet from the housing. At least a portion of the pusher is disposed within the actuation pathway and is moveable in a distal direction with respect to the housing. The housing and the pusher are collectively configured to limit movement of the distal end portion of the first portion of the housing towards the distal end portion of the second portion of the housing after delivery of the drug-containing tablet from the housing.

As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the words "a" or "an" and the phrase "one or more" may be used interchangeably.

As used herein, the words "proximal" and "distal" refer to direction closer to and away from, respectively, an operator of the drug delivery device. Thus, for example, the end of the dosage delivery device contacting or inserted into the patient's body (e.g. within the mouth) would be the distal end of the dosage delivery device, while the end opposite the distal end would be the proximal end of the dosage delivery device.

As used herein, the terms "about" and/or "approximately" when used in conjunction with numerical values and/or ranges generally refer to those numerical values and/or ranges near to a recited numerical value and/or range. For example, in some instances, "about 40 [units]" can mean within ±25% of 40 (e.g., from 30 to 50). In some instances, the terms "about" and "approximately" can mean within ±10% of the recited value. In other instances, the terms "about" and "approximately" can mean within ±9%, ±8%, ±7%, ±6%, ±5%, ±4%, ±3%, ±2%, ±1%, less than ±1%, or any other value or range of values therein or therebelow. The terms "about" and "approximately" may be used interchangeably.

In a similar manner, the term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. By way of another example, a structure defining a volume that is "substantially 0.50 milliliters (mL)" is intended to convey that, while the recited volume is desirable, some tolerances can occur when the volume is "substantially" the recited volume (e.g., 0.50 mL). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±1%, ±2%, ±3%, ±4%, ±5%, ±6%, ±7%, ±8%, ±9%, ±10%, or more of the stated geometric construction, numerical value, and/or range. Furthermore, although a numerical value modified by the term "substantially" can allow for and/or otherwise encompass a tolerance of the stated numerical value, it is not intended to exclude the exact numerical value stated.

While numerical ranges may be provided for certain quantities, it is to be understood that these ranges can include all subranges therein. Thus, the range "from 50 to 80" includes all possible ranges therein (e.g., 51-79, 52-78, 53-77, 54-76, 55-75, . . . , 70-79, etc.). Furthermore, all values within a given range may be an endpoint for the range encompassed thereby (e.g., the range 50-80 includes the ranges with endpoints such as 55-80, 50-75, etc.).

The dosage delivery devices (also referred to herein as "delivery devices" or "dispensing devices") described herein can be used, for example, for sublingual administration of a bioadhesive small volume sufentanil-containing drug dosage form. Such dosage forms can be any of the dosage forms shown and described in U.S. Pat. No. 8,753,308, entitled "Methods for Administering Small Volume Oral Transmucosal Dosage Forms Using a Dispensing Device," and/or U.S. Pat. No. 8,574,189, entitled "Storage and Dispensing Devices for Administration of Oral Transmucosal Dosage Forms," each of which is incorporated herein by reference in its entirety. Moreover, the delivery devices shown herein can include any of the structure and/or features of any of the delivery devices shown in U.S. Pat. No. 8,574,189, such as, for example, a housing defining an actuation pathway, a delivery member, a safety member (e.g., label) removably coupled to the housing, a deformable bridge member, or the like.

Figure 1B:
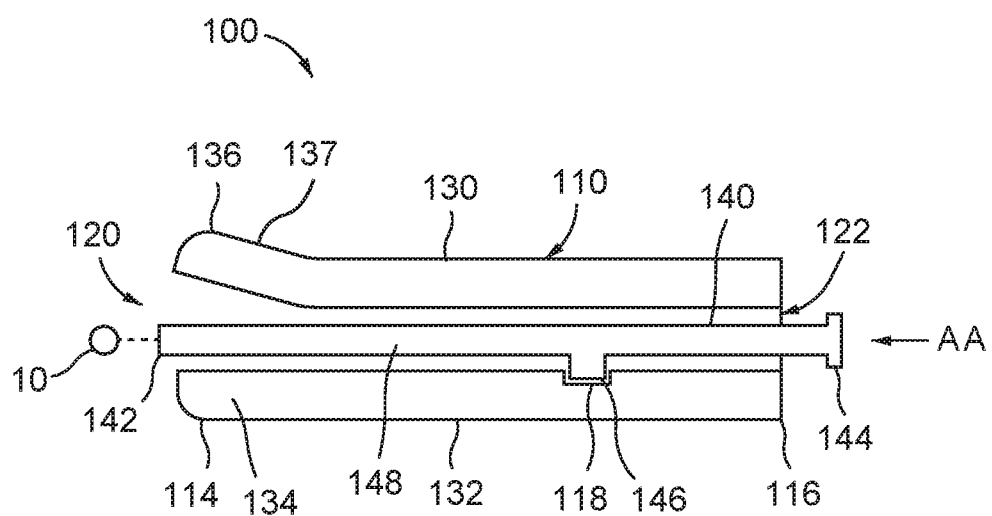

FIGS. 1A-1B are schematic illustrations of a dosage delivery device 100 according to an embodiment. The dosage delivery device 100 is configured to deliver a dosage form 10, such as a drug-containing tablet, to a subject, as described herein. In some embodiments, the dosage delivery device 100 can be a hand-held device configured to deliver the dosage form 10 to an oral mucosal membrane of a subject. More particularly, in some embodiments, the dosage delivery device 100 is configured to deliver the dosage form 10 to a sublingual mucosal membrane of the subject. In some embodiments, the dosage delivery device 100 is configured for a single use. For example, the delivery device can be a single dose applicator ("SDA") that contains a single drug or medication dose (e.g., a single dosage form) therein. More specifically, the delivery device 100 can be configured for only a single actuation to deliver a single dosage form to the subject. In this manner, the delivery device 100 can be characterized as a "one-time use" device, and therefore is disposable.

The dosage delivery device 100 includes a housing 110 and a pusher 140. The housing 110 defines an actuation pathway 112. The pusher 140 is coupled to the housing 110 such that at least a portion of the pusher 140 is disposed within the actuation pathway 112 defined by the housing 110. A distal end portion 114 of the housing 110 and a distal end portion 142 of the pusher 140 collectively define a volume 124 configured to contain or receive therein the dosage form 10.

The actuation pathway 112 of the housing 110 can be an elongate channel extended through at least a portion of the housing 110. As described in more detail herein, the actuation pathway 112 is configured to permit movement of the pusher 140 therein for delivery of the drug dosage form. In some embodiments, the actuation pathway 112 is in communication with an opening 122 at a first end portion of the housing, such as the proximal end portion 116 of the housing. The actuation pathway 112 can extend at least from the opening 122 at the proximal end portion 116 of the housing 110 to the volume 124 containing the dosage form. In some embodiments, before the device 100 is actuated, the actuation pathway 112 ends, or is closed at, a second end portion of the housing, such as the distal end portion 114 of the housing. During actuation of the device 100, the actuation pathway 112 can be extended, or opened, at the second end portion of the housing.

The actuation pathway 112 can have any suitable dimensions (e.g., height, width, diameter) for receiving the dosage form 10 and pusher 140 therein. One or more dimensions of the actuation pathway 112 can be configured to prevent the dosage form from turning, flipping or otherwise becoming improperly oriented within the actuation pathway. For example, a distance between opposing surfaces of portions of the housing 110 defining the actuation pathway 112 can be less than a diameter of the dosage form 10, thereby limiting rotational movement of the dosage form within the actuation pathway 112 (e.g., such that the dosage form is unable to turn or flip over within the actuation pathway).

In some embodiments, the pusher 140 has a first position in which at least a distal end portion 142 of the pusher 140 disposed within the actuation pathway 112 of the housing 110, as shown in FIG. 1A, and a second position in which at least the distal end portion 142 of the pusher 140 is not within the actuation pathway 112 of the housing 110, as shown in FIG. 1B. For example, in some embodiments, when the pusher 140 is in its second position, the distal end portion of the pusher is external to the actuation pathway 112 and/or the housing 110, and can be distal to the distal end portion 114 of the housing 110, as shown in FIG. 1B.

Movement of the pusher 140 from its first position to or towards its second position is configured to facilitate expelling the dosage form from the volume 124. The distal end portion 142 of the pusher 140 can have a contour or shape configured to engage (e.g., matingly engage) the dosage form 10 and can move the dosage form in a distal direction with respect to the volume as the pusher is moved to or towards its second position (i.e., in the distal direction with respect to the housing 110).

In some embodiments, the proximal end portion 144 of the pusher 140 is disposed external to the housing. For example, a portion of the pusher 140 can be disposed in and/or extended through the opening 122 defined by the first portion of the housing such that the proximal end portion 144 of the pusher 140 is external to and/or proximal to the proximal end portion 116 of the housing 110. In some embodiments, the proximal end portion 144 of the pusher 140 is external to the proximal end portion 116 of the housing 110 when the pusher 140 is in each of its first position and its second position, as shown in FIGS. 1A-1B.

In some embodiments, the proximal end portion of the pusher is a first distance from the proximal end portion 116 of the housing 110 when the pusher 140 is in its first position and is a second distance, less than the first distance, from the proximal end portion 116 of the housing when the pusher is in its second position. For example, in some embodiments, the proximal end portion 144 of the pusher 140 is proximally spaced apart from the proximal end portion 116 of the housing 110 when the pusher 140 is in its first position and the proximal end portion 144 of the pusher 140 is proximate to or in contact with the proximal end portion 116 of the housing 110 when the pusher 140 is in its second position. In some embodiments, a portion, such as the proximal end portion 144, of the pusher 140 can be in contact with an outer surface of the proximal end portion 116 of the housing 110 when the pusher is in its second position.

The pusher 140 is movable with respect to the housing 110. More specifically, the pusher 140 is moveable with respect to the housing 110 from its first position to its second position to expel the dosage form 10 from the volume 124. For example, the dosage delivery device 100 can be actuated by applying a force to the proximal end portion 144 of the pusher 140 to move the pusher 140 from its first position to its second position. The force can be applied, for example, in a distal direction (shown by arrow AA in FIGS. 1A-1B) by a hand or finger of an operator of the device 100. When the pusher 140 is moved to its second position, or in the distal direction with respect to the housing 110 towards the pusher's second position, the pusher can contact and expel the dosage form 10 from the volume 124 of the delivery device 100.

Although the pusher 140 is shown and described herein as having a first position and a second position, in some embodiments, the pusher can have three, four, or more positions. For example, in some embodiments, the pusher 140 can have a third position between its first position and its second position.

The dosage delivery device 100 has a first configuration in which the device 100 contains the dosage form 10 and is ready to be actuated for delivery of the dosage form. When the dosage delivery device 100 is in its first configuration, the pusher 140 is in the first position. The dosage delivery device 100 has a second configuration in which the dosage form 10 has been expelled from the device and the pusher is in the second position (or, in some embodiments, an intermediary position between the pusher's first position and second position). The device 100 can be configured such that it cannot return to its first configuration after the device is in its second configuration. Similarly stated, once the delivery device 100 is actuated, the delivery device 100 is locked in its second configuration. In this manner, the device 100 is configured to prevent a "used" device, from which the dosage form has been expelled, to be returned to a configuration in which the device 100 may appear to an observer to be an "unused" device assumed to contain a dosage form.

The housing 110 and the pusher 140 can be collectively configured (as described in more detail herein) to inhibit and/or limit movement of the pusher 140 in a proximal direction with respect to the housing 110. In some embodiments, when the delivery device is in its first configuration and the pusher is in its first position, the housing 110 and the pusher 140 are collectively configured to inhibit movement of the pusher in a proximal direction with respect to the housing. In some embodiments, when the delivery device is in its second configuration, the housing 110 and the pusher 140 are collectively configured to inhibit movement of the pusher 140 from its second position to its first position. Said another way, at least one of the housing 110 and the pusher 140 can be configured to inhibit and/or limit movement of the pusher 140 in a proximal direction with respect to the housing 110 after the delivery device 100 is in its second configuration. In this manner, the position of the pusher 140 with respect to the housing 110 and/or the configuration of the delivery device 100 each provides a visual indication to the observer regarding whether the dosage delivery device 100 is used or unused. In other words, an observer (e.g., the operator, subject, etc.) can determine that the dosage delivery device 100 is used (i.e., the dosage form 10 has been dispensed therefrom) by observing that the pusher 140 is in its second position and/or that the delivery device 100 is in the second configuration. Similarly, the observer can reliably presume that the dosage delivery device 100 is unused when the pusher 140 is in its first position and/or the delivery device 100 is in its first configuration.

The dosage delivery device 100 can include any suitable locking mechanism to prevent movement of the pusher 140 from its second position to or towards its first position with respect to the housing 110. For example, in some embodiments, the pusher 140 includes a retaining member 146. The retaining member 146 can be, for example, a protrusion extended from the pusher 140. In some embodiments, the retaining member 146 is biased away from an elongate body portion 148 of the pusher 140. For example, the retaining member 146 can be biased towards a surface of the actuation pathway 112.

The housing 110 can define at least one recess (or opening) 118 in communication with and/or defined by the actuation pathway 112. In some embodiments, the recess 118 is configured to receive at least a portion of the retaining member 146 when the pusher 140 is in its second position. In some embodiments, the recess 118 is configured to receive at least a portion of the retaining member 146 when the pusher 140 is between its first position and its second position. When a portion of the retaining member 146 is received in the recess 118, the pusher 140 is prevented from being moved in a proximal direction with respect to the housing. In this manner, an operator of the device 100 is unable to move or return the pusher 140 to its first position after actuation of the device 100 and delivery of the dosage form 10 therefrom. In use, this helps to ensure that the dosage delivery device 100, once used to deliver the dosage form 10, cannot intentionally or inadvertently be passed off as an unused (i.e., dosage form containing) device. In some embodiments, the retaining member 146 is biased such that, absent an opposing force, the retaining member 146 tends to move away from the body portion 148 of the pusher 140, towards the wall of the actuation pathway 122 and into the recess 118. Although the retaining member 146 and recess 118 work together to limit proximal movement of the pusher 140 with respect to the housing 110, the retaining member 146 and the recess 118 can be configured to not interfere with movement of the pusher 140 in the distal direction with respect to the housing 110.

Although the pusher 140 is illustrated and described herein as including one retaining member 146, in other embodiments, a dosage delivery device can include any suitable number of retaining members, such as two, three, four or more retaining members. Similarly, although the housing 110 is illustrated and described herein as including one recess or opening 118 configured to receive at least a portion of the retaining member 146, in other embodiments, a dosage delivery device can include any suitable number of recesses and/or openings configured to receive the retaining member(s) of a pusher, such as two, three, four or more recesses and/or openings.

In some embodiments, the delivery device 100 is configured to deform to produce an opening 120 through which the dosage form 10 is expelled from the volume 124 when the delivery device is moved from its first configuration to its second configuration. For example, in some embodiments, at least a portion of the housing 110 is configured to deform when the pusher 140 is moved with respect to the housing in the distal direction, as shown in FIG. 1B. Said another way, at least a portion of the housing 110 can be deformable such that the deformable portion 137 deforms (e.g., bends, curves, or otherwise moves) when the pusher 140 is moved from its first position to its second position. In this manner, the opening 120 is produced in the housing 110 from which the dosage form 10 can be expelled.

For example, in some embodiments, the housing 110 includes a first, or top, portion 130 and a second, or bottom, portion 132 that are coupled together (e.g., during manufacturing) to form the housing 110 and define the actuation pathway 112 therebetween. As used herein, references to portions of the device 100 as being the "top portion" or "bottom portion" or other similar positionally-oriented descriptors are made for the sake of clarity, and are not intended to imply that the device must be in a particular orientation for proper operation. For example, the device 100 can be properly operated to deliver a dosage form to a patient when the "top portion" of the housing 110 is oriented towards the patient's upper lip, lower lip, left side, and/or right side, and/or any orientation therebetween.

In some embodiments, the first and second portions 130, 132 are welded or otherwise permanently coupled together. In some embodiments, the first and second portions 130, 132 are removably coupled, such as with a snap-fit, complementary connectors, or a resistance fit. In some embodiments, the first and second portions 130, 132 are monolithically or integrally formed.

In some embodiments, a distal end portion 136 of the first portion 130 of the housing includes the deformable portion 137. In this manner, for example, the distal end portion 136 of the first portion 130 of the housing 110 can be configured to be deformed during actuation of the dosage delivery device 100. For example, when the delivery device 100 is in its first configuration, the distal end portion 136 of the first portion 130 is proximate to and/or in contact with a distal end portion 134 of the second portion 132. When the delivery device 100 is in its second configuration, the distal end portion 136 of the first portion 130 of the housing 110 is spaced apart from the distal end portion 134 of the second portion 132, for example, in response to movement of the pusher 140 in the distal direction (e.g., to or towards its second position). In some embodiments, the pusher 140 contacts an inner surface geometry (such as a ramp or protrusion; not shown in FIG. 1A or 1B) of the first portion 130 of the housing 110 when the pusher 140 is moved in the distal direction with respect to the housing such that the pusher 140 causes the distal end portion 136 of the first portion 130 to deform or move away from the distal end portion 134 of the second portion 132, thereby producing the opening 120 in the housing 110. In some embodiments, the material forming the distal end portion 136 is bent when the distal end portion 136 of the first portion is deformed or moved away from the distal end portion 134 of the second portion 132 of the housing 110. In some embodiments, the distal end portion 136 of the first portion 130 of the housing 110 is deformed such that the distal end portion of the first portion of the housing is angularly offset from the distal end portion 134 of the second portion 132 of the housing. In this manner, a non-zero angle is formed between the distal end portion 136 of the first portion 130 of the housing 110 and the distal end portion 134 of the second portion 132 of the housing when the distal end portion 136 of the first portion 130 of the housing 110 is deformed. For example, the angle can be within the range of 0.1 degrees to 90 degrees, within the range of 1 degree to 45 degrees, within the range of 1 degree to 10 degrees. In another example, in some embodiments, the angle can be about 1 degree, about 2 degrees, about 3 degrees, about 4 degrees, about 5 degrees, about 6 degrees, about 7 degrees, about 8 degrees, about 9 degrees, or about 10 degrees. For example, in some embodiments the angle is within a range of about 6 to about 7 degrees (e.g., about 6.6 or 6.7 degrees).

The distal end portion 136 can be permanently deformed upon actuation of the device 100 to deliver the dosage form 10 (e.g., when pusher 140 is moved to its second position). In some embodiments, for example, when the pusher 140 is in its second position, at least a portion of the pusher 140 is disposed within the actuation pathway 112 between the distal end portion 136 of the first portion 130 of the housing 110 and the distal end portion 134 of the second portion 132 of the housing 110 such that the pusher 140 inhibits or otherwise limits movement of the distal end portion 136 of the first portion 130 of the housing 110 towards the distal end portion 134 of the second portion 132. In this manner, the distal end portion 136 of the top portion 130 of the housing 110 is spaced apart from the distal end portion 134 of the bottom portion 132 of the housing and is inhibited by the pusher 140 from contacting or being moved towards or in closer proximity to the distal end portion 134 of the second portion 132 of the housing 110. Also in this manner, the distal end portion 136 of the top (or first) portion 130 of the housing is prevented from returning to its original position prior to actuation of the device 100 (e.g., to the position of the distal end portion 136 of the top portion 130 of the housing, when the delivery device 100 is in its first configuration).

Figure 1C:
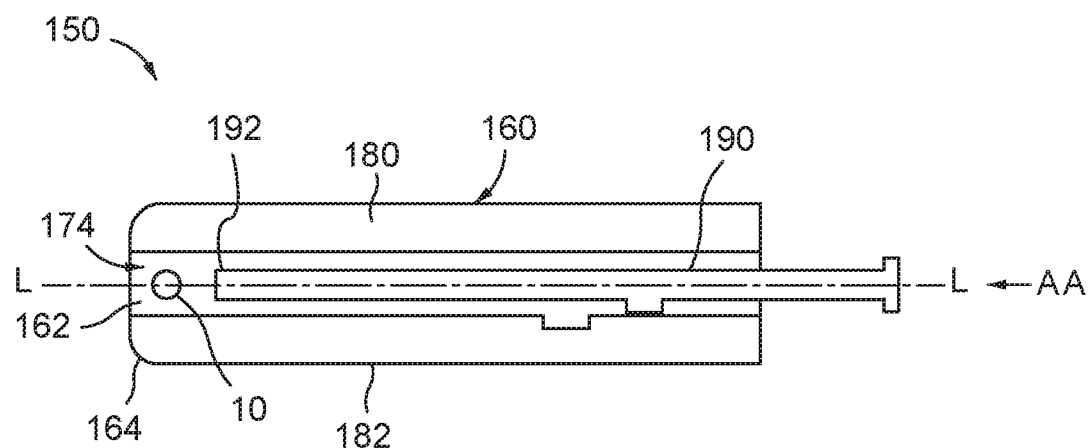
FIGS. 1C-1D are schematic illustrations of a dosage delivery device according to an embodiment, in a first configuration and a second configuration, respectively.
Figure 1D:
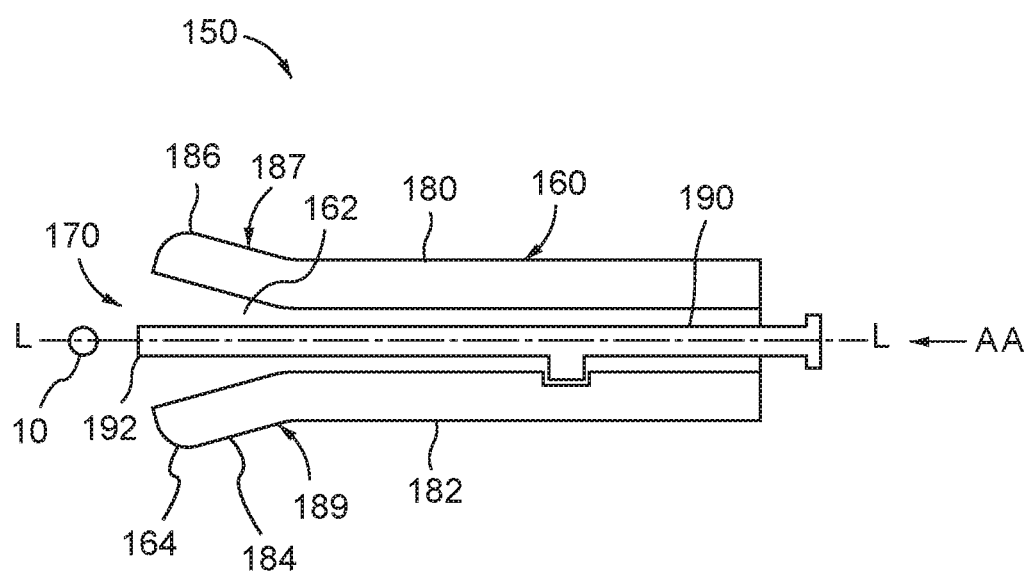

In some embodiments, as schematically shown in FIGS. 1C-1D, a dosage delivery device 150 according to an embodiment includes more than one deformable portion configured to produce an opening through which a dosage form can be expelled from the device. The dosage delivery device 150 can be similar, or identical, in many respects to the dosage delivery device 100, and so only certain differences therebetween are described in detail herein. The dosage delivery device 150 is configured to deliver the dosage form 10 to a subject, such as to an oral mucosal membrane of the subject, as described herein. The dosage delivery device 150 includes a housing 160 and a pusher 190. The housing 160 includes a first portion 180 and a second portion 182 and defines an actuation pathway 162 therebetween. The pusher 190 can be coupled to the housing 160 such that at least a portion of the pusher 190 is disposed within the actuation pathway 162 defined by the housing 160. A distal end portion 164 of the housing 160 and a distal end portion 192 of the pusher 190 collectively define a volume 174 configured to contain or receive therein the dosage form 10.

In some embodiments, the pusher 190 has a first position in which at least the distal end portion 192 of the pusher 190 is disposed within the actuation pathway 162 of the housing 160, as shown in FIG. 1C. The delivery device 150 is in a first configuration when the pusher 190 is in the first position. The pusher 190 has a second position in which at least the distal end portion 192 of the pusher 190 is not within the actuation pathway 162 of the housing 160, as shown in FIG. 1D. The delivery device 150 is in a second configuration when the pusher 190 is in the second position. The actuation pathway 162 is configured to permit movement of the pusher 190 therein for delivery of the drug dosage form therefrom. More specifically, movement of the pusher 190 from its first position to or towards its second position is configured to facilitate expelling the dosage form from the volume 124.

The delivery device 150 is configured to deform to produce an opening 170 through which the dosage form 10 is expelled from the volume 174 when the pusher 190 is moved from the first position to or towards the second position. For example, in some embodiments, at least a portion of the housing 160 is configured to deform when the pusher 190 is moved with respect to the housing in the distal direction, as shown in FIG. 1D. Said another way, at least a portion of the housing 160 can be deformable such that at least one portion of the housing deforms (e.g., bends, curves, or otherwise moves) when the pusher 190 is moved from its first position to its second position. In this manner, the opening 170 is produced in the housing 160 from which the dosage form 10 can be expelled.

In some embodiments, a distal end portion 186 of the first portion 180 of the housing 160 includes a first deformable portion 187 and a distal end portion 184 of the second portion 182 of the housing includes a second deformable portion 189. In this manner, for example, at least one of, or both of, the distal end portion 186 of the first portion 180 of the housing 160 and the distal end portion 184 of the second portion 182 of the housing can be deformed during actuation of the dosage delivery device 150. For example, when the dosage delivery device 150 is in its first configuration, the distal end portion 186 of the first portion 180 is proximate to and/or in contact with a distal end portion 184 of the second portion 182. When the delivery device 150 is in its second configuration, the distal end portion 186 of the first portion 180 of the housing 160 is spaced apart from the distal end portion 184 of the second portion 182, for example, in response to movement of the pusher 190 in the distal direction (e.g., to or towards its second position). In some embodiments, the pusher 190 contacts an inner surface geometry (such as a ramp or protrusion; not shown in FIG. 1C or 1D) of each of the first portion 180 of the housing 160 and the second portion 182 of the housing 160 when the pusher 190 is moved in the distal direction with respect to the housing such that the pusher 190 causes each of the distal end portion 186 of the first portion 180 of the housing and the distal end portion 184 of the second portion 182 of the housing to deform or move away from each other (or, said another way, away from a longitudinal axis L of the actuation pathway 162), as shown in FIG. 1D, thereby producing the opening 170 in the housing 160. In some embodiments, the material forming the distal end portions 184, 186 is bent when each distal end portion 184, 186 is deformed as described herein.

In some embodiments, the distal end portion 186 of the first portion 180 of the housing 160 is deformed such that the distal end portion of the first portion of the housing is angularly offset from the longitudinal axis L of the actuation pathway. In this manner, a non-zero angle is formed between the distal end portion 186 of the first portion 180 of the housing 160 and the longitudinal axis L of the actuation pathway 162 of the housing when the distal end portion 186 of the first portion 180 of the housing 160 is deformed. For example, the angle can be within the range of 0.1 degrees to 90 degrees, within the range of 1 degree to 45 degrees, or within the range of 1 degree to 10 degrees. In another example, the angle can be about 1 degree, about 2 degrees, about 3 degrees, about 4 degrees, about 5 degrees, about 6 degrees, about 7 degrees, about 8 degrees, about 9 degrees, or about 10 degrees. For example, in some embodiments the angle is within a range of about 6 to about 7 degrees (e.g., about 6.6 or 6.7 degrees). In some embodiments, the distal end portion 184 of the second portion 182 of the housing 160 is deformed such that the distal end portion of the second portion of the housing is angularly offset from the longitudinal axis L of the actuation pathway. In this manner, a non-zero angle is formed between the distal end portion 184 of the second portion 182 of the housing 160 and the longitudinal axis L of the actuation pathway 162 of the housing when the distal end portion 184 of the second portion 182 of the housing 160 is deformed. For example, the angle can be within the range of 0.1 degrees to 90 degrees, within the range of 1 degree to 45 degrees, or within the range of 1 degree to 10 degrees. In another example, the angle can be about 1 degree, about 2 degrees, about 3 degrees, about 4 degrees, about 5 degrees, about 6 degrees, about 7 degrees, about 8 degrees, about 9 degrees, or about 10 degrees. For example, in some embodiments the angle is within a range of about 6 to about 7 degrees (e.g., about 6.6 or 6.7 degrees).

At least one of the distal end portions 184, 186 can be permanently deformed upon actuation of the device 150 to deliver the dosage form 10 (e.g., when pusher 190 is moved to its second position). In some embodiments, for example, when the pusher 190 is in its second position, at least a portion of the pusher 190 is disposed within the actuation pathway 162 between the distal end portion 186 of the first portion 180 of the housing 160 and the distal end portion 184 of the second portion 182 of the housing 160 such that the pusher 190 inhibits or otherwise limits movement of the distal end portion 186 of the first portion 180 of the housing 160 and the distal end portion 184 of the second portion 182 of the housing towards each other. In this manner, the distal end portion 186 of the top portion 180 of the housing 160 and the distal end portion 184 of the bottom portion 182 of the housing are spaced apart and inhibited by the pusher 190 from contacting or being moved towards or in closer proximity to the opposing distal end portion 184, 186. Also in this manner, the distal end portions 134, 136 can be prevented from returning to the distal end portion's respective original position prior to actuation of the device 150 (e.g., when the delivery device 100 is in its first configuration).

A dosage delivery device 200 according to an embodiment is shown in FIGS. 2-8. The delivery device 200 includes a housing 210, a pusher 240, a dosage form 20 and a locking member 280. The dosage delivery device 200 is a hand-held and manually operable device configured to deliver the dosage form 20 to a subject, as described herein. The dosage form 20 can be, for example, a drug-containing tablet. In some embodiments, the dosage form 20 can include a dosage of a pain-relieving medicament, such as sufentanil.

The dosage delivery device 200 is configured to deliver the dosage form 20 to an oral mucosal membrane of a subject. More particularly, in some embodiments, the delivery device 200 can be configured to deliver the dosage form 20 to a sublingual mucosal membrane of the subject. In some embodiments, the dosage delivery device 200 is configured for a single use. In other words, the delivery device 200 can be configured for only a single actuation to deliver a single dosage form to the subject. Components of the dosage delivery device 200 can be identical to or similar in many respects to components of any dosage delivery device 100, 150 described herein.

Figure 2:
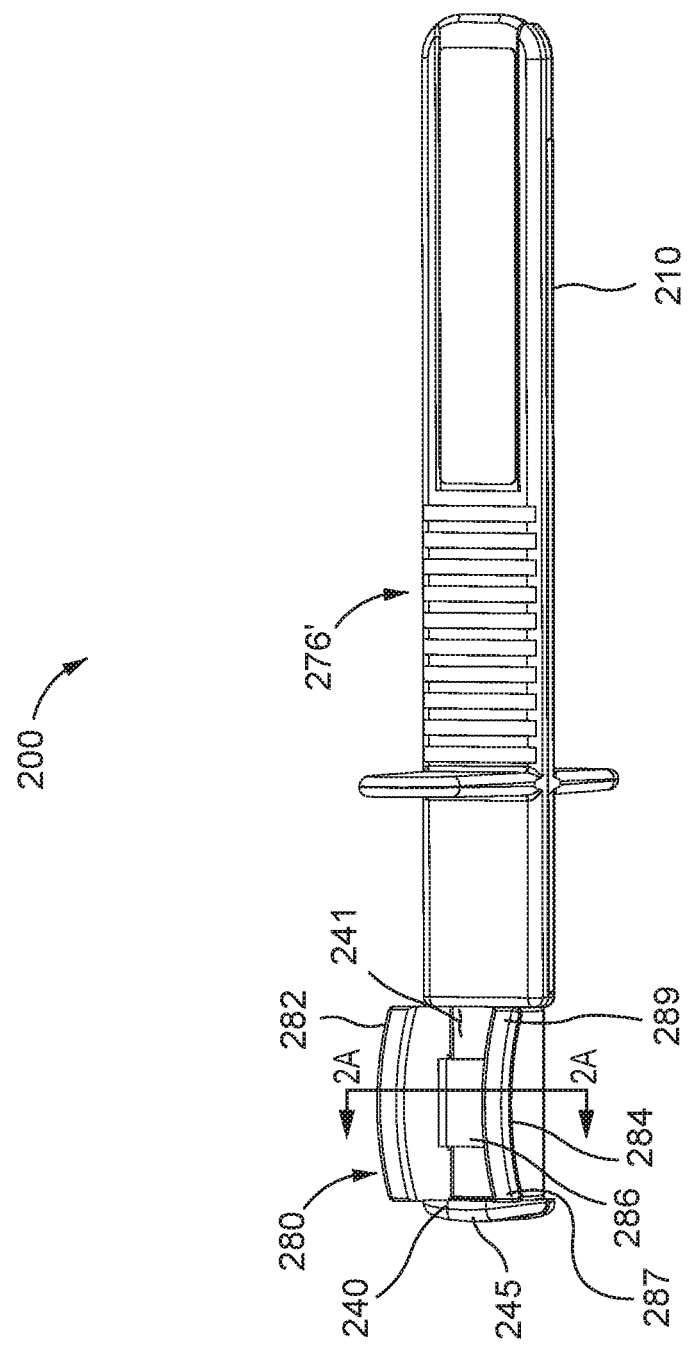
FIG. 2 is a bottom perspective view of a dosage delivery device according to an embodiment.
Figure 3:
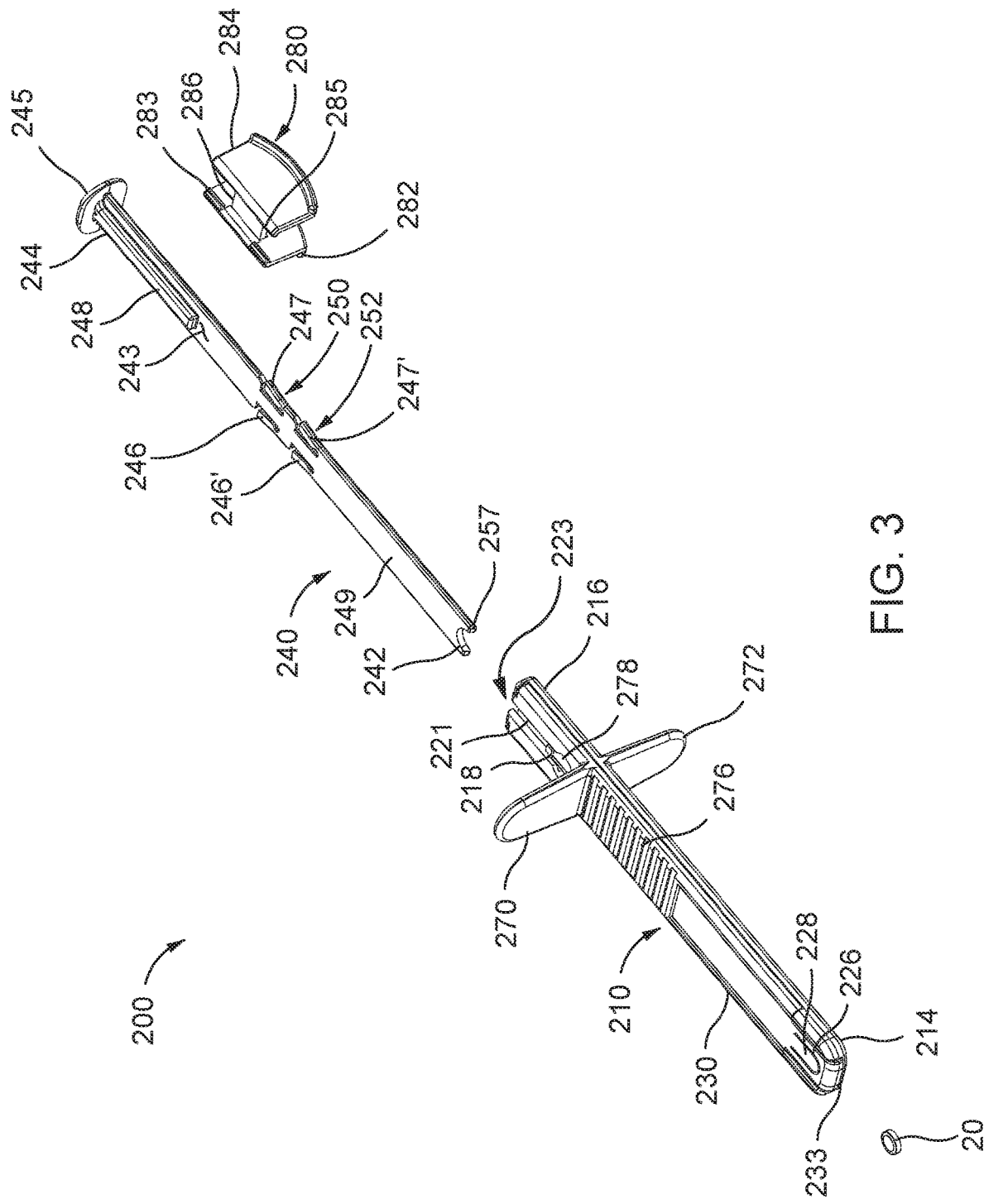
FIG. 3 is an exploded view of the dosage delivery device of FIG. 2.

The housing 210 is elongate in form and includes a top portion 230 (shown in FIG. 2) and a bottom portion 232 (shown in FIG. 3). The top and bottom portions 230, 232 of the housing 210 can be coupled together using any suitable mechanism described herein. The top and bottom portions 230, 232 of the housing 210 define an actuation pathway 212 therebetween. The actuation pathway 212 is a pathway within which a portion of the pusher 240 moves during dispensation of the dosage form 20 from the delivery device 200. A distance between a surface of the top portion 230 of the housing and the bottom portion 232 of the housing 210 can be less than a diameter of the dosage form 20, thereby limiting rotational movement of the dosage form 20 within the actuation pathway 212 (e.g., such that the dosage form is unable to turn or flip over within the actuation pathway) during such dispensation.

Figure 4:
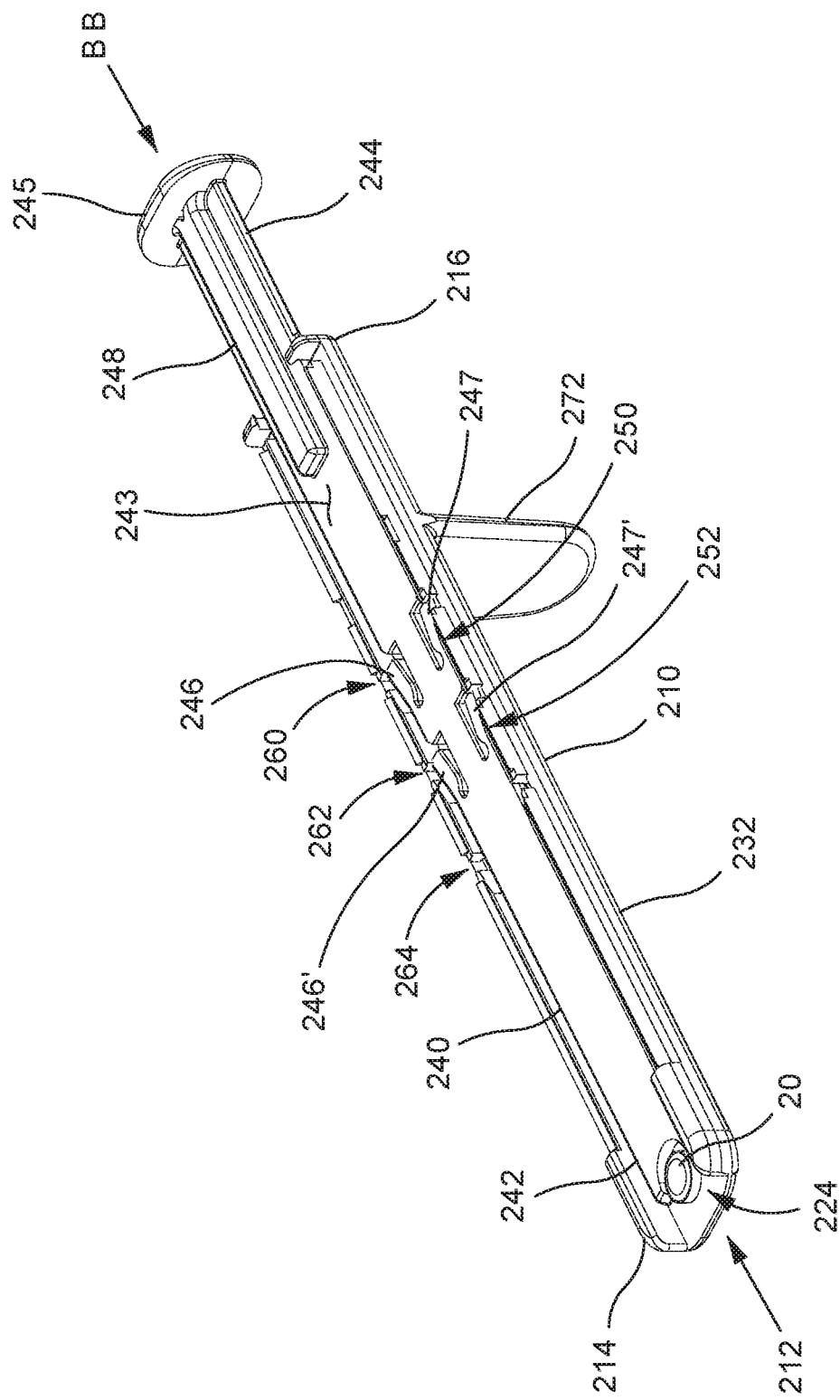
FIGS. 4 and 5 are perspective views of a portion of the dosage delivery device of FIG. 2 in a first configuration and a second configuration, respectively.
Figure 5:
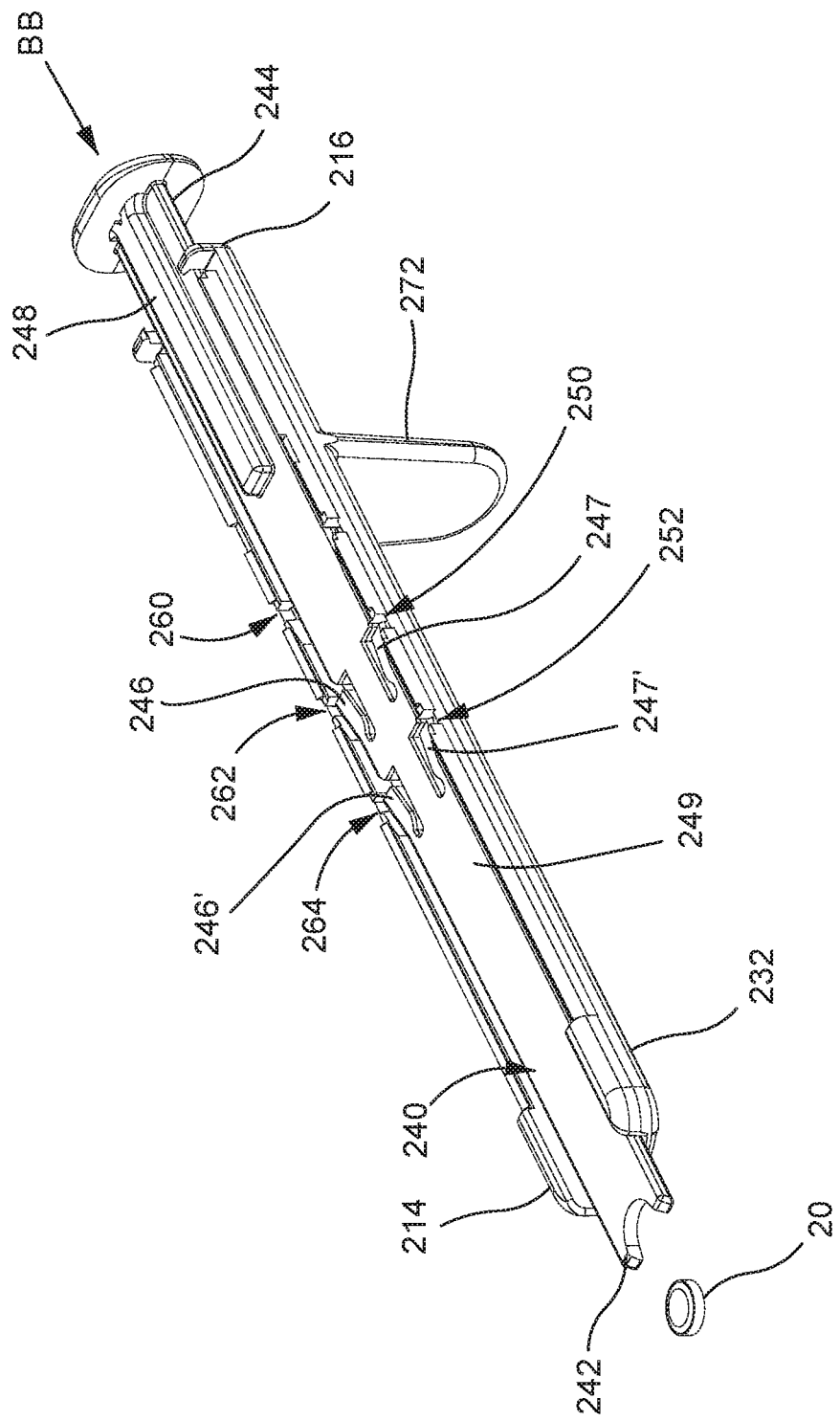

The pusher 240 is coupled to the housing 210 such that at least a portion of the pusher 240 is disposed within the actuation pathway 212. The pusher 240 is movable within the actuation pathway 212, such that the pusher 210 can move therein to expel the dosage form 20 from the delivery device 200. More particularly, before the delivery device 200 is actuated, the pusher 240 is in a first position such that a distal end portion 242 of the pusher 240 is disposed within the actuation pathway 212 and a proximal end portion 244 of the pusher is disposed external to and proximally spaced apart by a first distance from the proximal end portion 216 of the housing 210, as shown in FIG. 4. During actuation of the delivery device 200, the pusher 240 is moved in a distal direction, shown by arrow BB in FIG. 4, with respect to the delivery device 200. After actuation, the pusher 240 is in a second position such that the distal end portion 242 of the pusher 240 is external to and distally disposed with respect to the distal end portion 214 of the housing, and the proximal end portion 244 of the pusher is external to and proximally spaced apart by a second distance, less than the first distance, from the proximal end portion 216 of the housing 210, as shown in FIG. 5.

In some embodiments, the delivery device 200 includes one or more mechanisms to prevent inadvertent actuation of the delivery device 200. Referring to FIGS. 2 and 3, the delivery device 200 includes the locking member 280, which can be removably coupled to the pusher 240 and is configured to prevent actuation of the delivery device 200. More specifically, the locking member 280 is configured to inhibit or limit movement of the pusher 240 in the distal direction (e.g., from its first position to or towards its second position) when the locking member is coupled to the pusher 240. The locking member 280 includes a first side portion 282, a second side portion 284, and a bridge 286 extending between the first side portion and the second side portion. The bridge 286 is coupled at opposing ends to the side portions 282, 284, and acts as a flexible hinge.

Figure 2A:
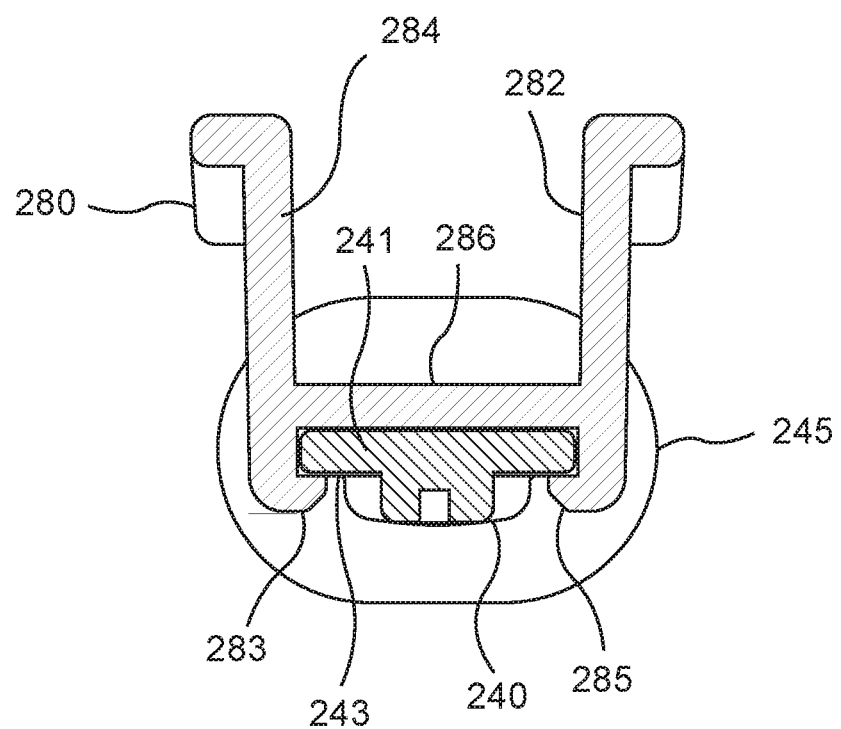
FIG. 2A is a cross-sectional view of the dosage delivery device of FIG. 2 taken along line 2A-2A

The locking member 280 is configured to be at least partially disposed about a portion of the pusher 240. For example, as shown in FIGS. 2 and 2A, the locking member 280 is partially disposed about a proximal end portion 244 of the pusher 240 such that the locking member 280 is in contact with a first (e.g., bottom) surface 241 of the pusher 240 and such that flanges 283, 285 of each of the first and second side portions 282, 284, respectively, are partially disposed about the proximal end portion 244 of the pusher and are in contact with a second (e.g., top) surface 243 of the pusher. When the locking member 280 is coupled to the pusher 240, a proximal end 287 of the locking member 280 is proximate to and/or engaged with an end cap 245 of the pusher 240 and/or a distal end 289 of the locking member is proximate to and/or engaged with a face (not shown) of the proximal end portion 216 of the housing 210, as shown in FIG. 2. Said another way, the locking member 280 can have a length substantially equal to the first distance between the proximal end portion 244 of the pusher 240 and the proximal end portion 216 of the housing 210. In this manner, the locking member 280 prevents movement of the pusher 240 when the pusher is in its first position and the locking member 280 is coupled thereto. Additionally, because the length of the locking member 280 is greater than the distance between the proximal end portion 244 of the pusher 240 and the proximal end portion 216 of the housing 210 when the pusher is in its second position, the locking member 280 is prevented from being recoupled to the pusher 240 after actuation of the delivery device 200.

The first and second side portions 282, 284 of the locking member 280 are configured to be moved towards each other to flex the bridge 286 and move the flanges 283, 285, respectively, away from each other, thus opening the locking member such that the flanges can be removed from about the pusher 240. Although the locking member 280 is illustrated and described herein as being completely separable from the pusher 240, in other embodiments, a locking member can be coupled to the pusher and/or housing, such as via a tether, after removal from being disposed about the proximal end portion of the pusher. With the locking member 280 removed, the pusher 240 can be moved in a distal direction, shown by arrow BB in FIG. 4, with respect to the housing 210 from its first position to its second position.

In another example of mechanisms to prevent inadvertent actuation of the delivery device 200, the device can include a breakable member that inhibits or limits movement of the pusher in the distal direction with respect to the housing (e.g., from the pusher's first position to or towards its second position). For example, returning to FIG. 3, the pusher 240 includes an elongate protrusion 248 disposed on the top surface 243 of the proximal end portion 244 of the pusher 240. The elongate protrusion 248 can be configured to engage a bridge (or breakable member) 218 of the housing 210. The bridge 218 is disposed within a channel 221 defined by the housing, such as by the proximal end portion 216 of the housing. The channel 221 of the housing can be in communication with the actuation pathway 212. The bridge 218 is configured to prevent movement of the pusher 240 in the distal direction absent a sufficient actuation force, as described herein.

When the pusher 240 is moved in the distal direction with respect to the delivery device (e.g., from the pusher's first position to or towards its second position) in response to a sufficient actuation force (as opposed to a lesser or de minimis amount of force resulting from, for example, an inadvertent contact with the pusher or an abandoned actuation attempt), the elongate protrusion 248 slidably moves in a distal direction within the channel 221 until the protrusion 248 engages and presses upon the bridge 218 with sufficient force such that the bridge is at least partially separated from the housing 210. In some embodiments, the bridge 218 remains attached to the housing 210 at or by at least a corner portion of the bridge, and the bridge can rotate or otherwise move about the attachment location such that the bridge is at least partially removed or otherwise displaced from the channel 221. In other embodiments, the bridge 218 can be wholly separated from the housing 210 during actuation of the delivery device 200. The housing 210 (e.g., an inner surface of the top portion 230 of the housing 210) can define a recess 222 adjacent the channel 221. The recess 222 can be configured to receive at least a portion of the bridge 218 when the bridge is at least partially separated from the housing 210. In this manner, the elongate protrusion 248 can continue to move in the distal direction within the channel 221 when the pusher 240 is moved to or towards its second position.

Returning to FIG. 4, the distal end portion 242 of the pusher 240 is configured to contact the dosage form 20 for delivery of the dosage form from the delivery device 200. As shown, the distal end portion 242 of the pusher 240 is contoured and/or shaped to receive and/or matingly engage the dosage form 20. In other embodiments, however, the distal end portion 242 of the pusher 40 can have any suitable contour and/or shape for conveying or expelling the dosage form 20 from the delivery device 200. Further, the distal end portion 214 of the housing 210 and the distal end portion 242 of the pusher 240 are shaped to collectively define a volume 224 configured to contain the dosage form 20, e.g., within the actuation pathway 212.

In some embodiments, the delivery device 200 is configured to deform to produce an opening through which the dosage form 20 can be expelled from the volume 224 during actuation of the delivery device 200. When the delivery device 200 is in its first configuration, the distal end portion 236 of the top portion 230 of the housing 210 is proximate to and/or in contact with a distal end portion 234 of the bottom portion 232 of the housing 210. In some embodiments, an outer surface of the distal end portion 236 of the top portion 230 of the housing 210 is substantially parallel to an opposing outer surface of the distal end portion 234 of the bottom portion 232 of the housing 210 when the delivery device 200 is in its first configuration. When the delivery device 200 is in its second configuration, the distal end portion 236 of the top portion 230 is spaced apart from the distal end portion 234 of the bottom portion 232, for example, in response to movement of the pusher 240 in the distal direction (e.g., to or towards the pusher's second position).

For example, the delivery device 200 is configured such that, when the pusher 240 is moved from its first position to or towards its second position, a portion of the pusher 240 (e.g., the distal end portion 242 of the pusher) contacts and presses upon a lower (or inner) surface 231 of the top portion 230 of the housing 210. More specifically, in some embodiments, the pusher 240 contacts an inner surface geometry 237 (such as a ramp, slope or protrusion) (shown, for example, in FIG. 6), described in more detail herein, of the deformable distal end portion 236 of the top portion 230 housing 210 when the pusher 240 is moved in the distal direction with respect to the housing such that the pusher 240 causes the distal end portion 236 of the top portion 230 to deform or move away from the distal end portion 234 of the bottom portion 232, thereby producing the opening 220 in the housing 210.

In response to the pressure exerted upon the inner surface geometry 237 of the deformable distal end portion 236 of the top portion 230 of the housing 210, the distal end portion 236 deforms (e.g., bends, deflects, or otherwise moves) away from the distal end portion 234 of the bottom portion 232 of the housing 210 to produce the opening 220. In some embodiments, the distal end portion 236 of the top portion 230 of the housing 210 is deformed such that the distal end portion of the top portion of the housing is angularly offset from the distal end portion 234 of the bottom portion 232 of the housing. In this manner, a non-zero angle is formed between the distal end portion 236 of the first portion 230 of the housing 210 and the distal end portion 234 of the second portion 232 of the housing when the distal end portion 236 of the first portion 230 of the housing 210 is deformed. For example, the angle can be within the range of 0.1 degrees to 90 degrees, within the range of 1 degree to 45 degrees, within the range of 1 degree to 10 degrees. In another example, in some embodiments, the angle can be about 1 degree, about 2 degrees, about 3 degrees, about 4 degrees, about 5 degrees, about 6 degrees, about 7 degrees, about 8 degrees, about 9 degrees, or about 10 degrees. For example, in some embodiments the angle is within a range of about 6 to about 7 degrees (e.g., about 6.6 or 6.7 degrees).

Although the dosage delivery device 200 is shown and described herein as having a distal end portion 236 of the top portion 230 of the housing 210 that is deformable, in other embodiments a different portion of the housing 210 can be deformable. For example, in some embodiments a distal end portion 236 of the bottom portion 232 of the housing 210 can be deformable in a manner similar to that described herein (e.g., with respect to distal end portion 186 of the second portion 182 of the housing 160 of delivery device 250). In some embodiments, a delivery device can include a housing with a deformable portion distinct from either the first or top portion and the second or bottom portion. For example, a delivery device can include a housing with a deformable distal end cap.

As actuation of the delivery device 200 is continued, and the pusher 240 is moved further towards its second position, at least a portion of the distal end portion 242 of the pusher 240 can be extended from the opening 220 and at least a portion of the pusher (e.g., at least a portion of the distal end portion of the pusher) is disposed between the distal end portions 236, 234 of the top and bottom portions 230, 232, respectively, of the housing 210.

The distal end portion 236 can be permanently deformed upon actuation of the device 200 and delivery of the dosage form 20 (e.g., when pusher 240 is moved to its second position). In some embodiments, for example, when the pusher 240 is in its second position, at least a portion of the pusher 240 is disposed within the actuation pathway 212 between the distal end portion 236 of the top portion 230 of the housing 210 and the distal end portion 234 of the bottom portion 232 of the housing 210 such that the pusher 240 inhibits or otherwise limits movement of the distal end portion 236 of the top portion 230 towards the distal end portion 234 of the bottom portion 232. In this manner, the distal end portion 236 of the top portion 230 of the housing 210 is spaced apart from the distal end portion 234 of the bottom portion 232 of the housing and is inhibited by the pusher 240 from contacting or being moved towards or in closer proximity to the distal end portion 234 of the bottom portion 232 of the housing 210.

Figure 6:
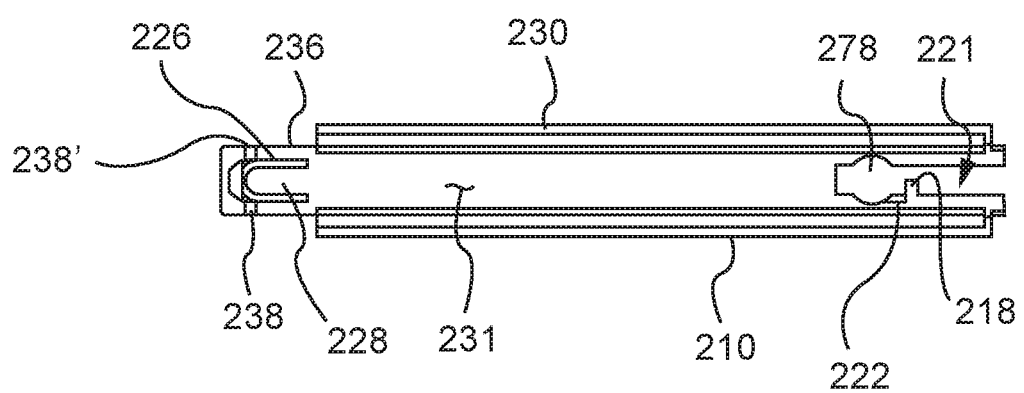
FIG. 6 is a bottom view of a portion of the dosage delivery device of FIG. 2.

In some embodiments, as shown in FIGS. 3 and 6, the distal end portion 236 of the top portion 230 of the housing 210 includes an aperture 226, which can be configured to facilitate deformation of the distal end portion 236 of the top portion 230 of the housing 210. For example, as shown, the top portion 230 of the housing 210 defines a curved or U-shaped aperture 226. A cantilevered portion 228 of the housing 210, described in more detail herein, extends into the curve or "U" of the aperture 226. The portions of the top portion 230 of the housing 210 on either side of the ends of the aperture (e.g., free ends of the curve or "U") act as hinges to facilitate deformation of the distal end portion of the top portion 230 of the housing away from the distal end portion 234 of the bottom portion 232 of the housing 210.

Figure 3A:
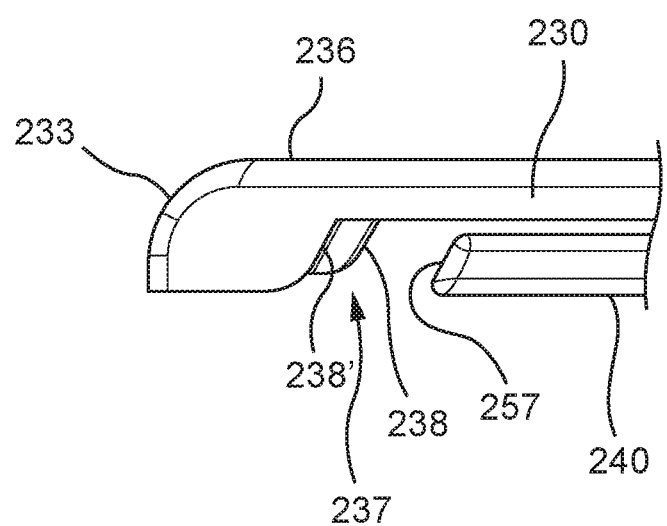
FIG. 3A is a side view of a portion of the dosage delivery device of FIG. 2.

In some embodiments, as shown in FIGS. 3 and 3A, an outer surface 233 of the distal end portion 236 of the top portion 230 of the housing 210 curves downwardly towards the distal end portion 234 of the bottom portion 232 of the housing 210. This downwardly curved portion can be characterized as a nose portion 233. The nose portion 233 can include downwardly extending side walls on either side, each of which has a sloped, curved, or otherwise angled proximal end face 238, 238' (as shown in FIGS. 3, 3A and 6). The end face 238, 238' can include at least a portion of the inner surface geometry 237 configured to be contacted or engaged by the pusher 240, as described above. A distal end face 257 of the pusher 240 can have a complementary slope, angle, or shape to reduce friction from engagement of the pusher 240 with the proximal end faces 238, 238' of the side walls of the nose portion 233 of the housing 210 during actuation. When the pusher 240 engages the sloped portions 238 of the top portion 230 of the housing, the nose portion 233 is moved away from the bottom portion 232 of the housing 210, thereby forming the opening and exposing the cantilevered portion 228 of the housing 210. In some embodiments, after actuation and deformation of the distal end portion 236 of the top portion 230 of the housing 210, the side walls of the nose portion 233 of top portion 230 of the housing 210 are configured to engage an upper surface of the pusher 240, thereby preventing or limiting movement of the distal end portion 236 of the top portion 230 of the housing 210 towards the distal end portion 234 of the bottom portion 232 of the housing 210.

Figure 7:
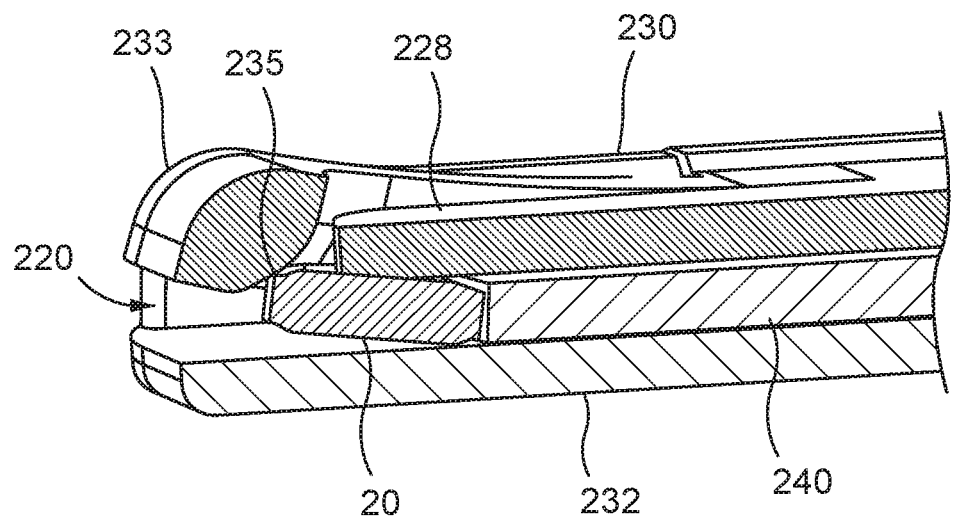
FIGS. 7 and 8 are cross-sectional views of a distal end portion of the dosage delivery device of FIG. 2 showing surface geometries of a portion of a housing of the device according to various embodiments.
Figure 8:
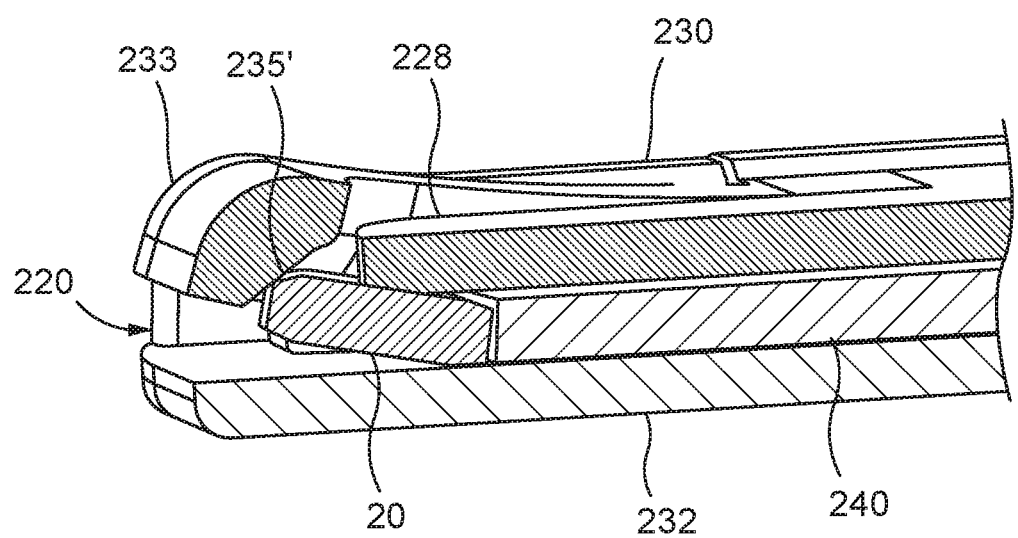

In some embodiments, as shown in FIGS. 7 and 8, the inner surface of the nose portion 233 is contoured or shaped to limit rotation of the dosage form 20 with respect to the housing 210 as the dosage form is being expelled (or delivered) from the device 200. For example, in some embodiments, an inner surface 235 of the nose portion 233 is curved (e.g., is in the shape of a convex curve), such that the dosage form 20 engages the curved inner surface 235 during delivery, as shown in FIG. 7. In another example, an inner surface 235' of the nose portion 233 is angled to engage a surface (e.g., an upper surface) of the dosage form 20 during delivery, as shown in FIG. 8.

In some circumstances, as the pusher 240 moves the dosage form 20 towards the opening 220, the force exerted upon the dosage form 20 by the pusher 240 can cause the dosage form 20 to rotate or lift with respect to the housing 210 (e.g., such that at least one of a leading edge or a trailing edge of the dosage form 20 becomes spaced apart from the bottom portion 232 of the housing as shown in FIGS. 7 and 8, and/or such that the dosage form 20 turns sideways). Rotation of the dosage form 20 with respect to the housing 210 can affect the speed at which the dosage form 20 is expelled through the opening 220, and expelling the dosage form 20 at a different (e.g., higher) speed than that which the delivery device is intended to produce can interfere with proper delivery of the dosage form to the patient. For example, if a dosage form 20 is expelled too quickly from the delivery device, it may inadvertently be propelled towards the throat of the user instead of an oral mucosal membrane.

The contoured or curved (e.g., convex) inner surface 235 (or 235') of the nose portion 233 is configured to limit the degree to which the dosage form 20 can rotate with respect to the housing 210 before the dosage form 20 is expelled through the opening 220, and thus prevent expelling the dosage form 20 at such higher speeds. The convex curved geometry shown in FIG. 7, however, in some embodiments, acts to limit rotation of the dosage form 20 to a greater degree than the angled geometry shown in FIG. 8. Although angled and convex inner surfaces 235', 235, respectively, of the nose portion 233 are illustrated and described herein, in other embodiments, the inner surface of the nose portion 233 can have any suitable shape or geometry configured to limit rotation of the dosage form 20 with respect to the housing during delivery of the dosage form from the delivery device. In some embodiments, the cantilevered portion 228 of the housing 210 can also act to limit rotation of the dosage form 20 with respect to the housing 210.

As discussed above, in some embodiments, the delivery device 200 is configured for only a single actuation to dispense a single dosage form 20 (or a single dosage of medicament). As such, the delivery device 200 can include one or more tamper-resistant mechanisms. For example, in some embodiments, the delivery device 200 is configured to prevent removal of the dosage form 20 from the delivery device without actuating the device such that the device would appear "unused" when it is devoid of the dosage form. In another example, the delivery device 200 can be configured to prevent movement of the delivery device to its first configuration (e.g., in which the pusher is in its first position) after the delivery device is in its second configuration (e.g., in which the pusher is in its second position). Said another way, the delivery device includes one or more mechanisms to prevent a "used" device from being tampered with or otherwise altered or reconfigured to resemble an "unused" device.

For example, the pusher 240 can include one or more retaining members 246, 246', 247, 247' configured to limit and/or inhibit movement of the pusher in a proximal direction with respect to the housing. Similarly stated, the pusher 240 can include one or more retaining members 246 configured to prevent the pusher being moved from its second position to its first position. The retaining member 246 can be, for example, a protrusion extended from the pusher 240.

As shown in FIGS. 3-5, the pusher includes a first set 250 of retaining members disposed at a first location of the elongate body portion 249 of the pusher 240. The first set 250 of retaining members includes a first retaining member 246 extended from a first side of the pusher 240 and a second retaining member 247 extended from a second side of the pusher opposite the first side. The pusher 240 includes a second set 252 of retaining members disposed at a second location of the elongate body portion 249 of the pusher. The second set 252 of retaining members includes a third retaining member 246' extended from the first side of the pusher 240 and a fourth retaining member 247' extended from the second side of the pusher. As shown, the first and second locations of the sets 250, 252 of retaining members are disposed distally with respect to a distal end of the elongate protrusion 248 of the pusher 240. In some embodiments, the first and second locations are at a middle portion of the pusher 240 between its distal end portion 242 and its proximal end portion 244. Also as shown, the first and second locations are distal to the protrusions 270, 272 extended from the housing 210 when the pusher 240 is in its first position. The second location of the pusher's body portion 249 can be distal to the first location. A free end of each retaining member 246, 246', 247, 247' can be outwardly biased, i.e., in a direction away from a centerline (not shown) of the pusher 240. Said another way, the retaining members can each be biased towards a surface of the actuation pathway 212. The retaining members are configured to flex inwardly towards a centerline of the pusher 240 when the pusher is moved in the distal direction with respect to the housing 210 when constrained within the actuation pathway 212. The retaining members 246, 246', 247, 247' can be configured to flex or otherwise move outwardly when no longer constrained, as described herein.

Referring to FIG. 4, the housing 210 (e.g., the bottom portion 232 of the housing) defines one or more sets of recesses (or openings). As shown, the housing defines a first set 260 of recesses, a second set 262 of recesses, and a third set 264 of recesses. Each recess (or opening) is in communication with the actuation pathway 212 and is configured to receive at least a portion of one or more of the retaining members. At least one retaining member 246, 246', 247, 247' is biased such that, when the at least one retaining member is aligned with or otherwise collocated with a recess, the retaining member flexes or otherwise moves outwardly due to a bias of the retaining member and such that at least a portion of the at least one retaining member is received in the respective recess. In some embodiments, each recess has a shoulder portion configured to contact or otherwise engage a portion of a free end of the retaining member received therein. When at least a portion of at least one retaining member is received in at least one of the housing 210 recesses, movement of the pusher in the proximal direction with respect to the housing 210 is inhibited.

When the pusher is in its first position with respect to the housing, the first set 250 of retaining members can be at least partially received in the first set 260 of recesses and the second set 252 of retaining members can be at least partially received in the second set 262 of recesses, as shown in FIG. 4. In this manner, proximal movement of the pusher 240 with respect to the housing 210 is prevented or limited when the pusher is in its first position. As such, the delivery device 200 is configured to prevent removal of the pusher 240 from the housing 210 in the proximal direction.

When the pusher is in its second position with respect to the housing, the first set 250 of retaining members can be at least partially received in the second set 262 of recesses and the second set 252 of retaining members can be at least partially received in the third set 264 of recesses, as shown in FIG. 5. In this manner, proximal movement of the pusher 240 with respect to the housing 210 is prevented when the pusher is in its second position. As such, the delivery device 200 is configured to prevent the pusher 240 from being moved or returned to its first position after actuation and delivery of the dosage form 20 from the device.

Also, in this manner, the housing 210 and the pusher 240 are collectively configured to limit movement of the distal end portion of the top portion of the housing 210 towards the distal end portion of the bottom portion of the housing 210 after delivery of the dosage form from the housing 210. More specifically, because the pusher 240 is prevented by the retaining members from moving from the pusher's second position to or towards its first position, the distal end portion 242 of the pusher remains disposed between the distal end portion 236 of the top portion 230 of the housing 210 and the distal end portion 234 of the bottom portion 232 of the housing 210, thus inhibiting or limiting movement of the distal end portion of the top portion of the housing 210 to or towards the distal end portion of the bottom portion of the housing 210. Similarly stated, the distal end portion of the pusher 240 retains the top portion of the housing 210 in its deformed state (e.g., such that the distal end portion of the top portion of the housing is moved away from the distal end portion of the bottom portion of the housing) after actuation of the delivery device 200.

Although the pusher 240 is illustrated and described herein as including sets 250, 252 of retaining members, and that each set includes a retaining member on opposing sides of the pusher, in other embodiments, one or more retaining members can be differently positioned with respect to the pusher's elongate body portion 249. For example, in some embodiments, a delivery device includes a pusher having retaining members only on a first side or from a single surface of the pusher's elongate body portion 249. In other embodiments, one or more retaining members can extend from an upper surface of the pusher and/or a lower surface of the pusher.

Similarly, although the housing is illustrated and described herein as including sets 260, 262, 264 of recesses, and that each set includes a recess on opposing sides of the actuation pathway, in other embodiments, one or more recesses can be defined at or by different locations of the housing. For example, in some embodiments, a delivery device includes a housing defining recesses or openings only on a first side or by a single surface of the housing. In other embodiments, the top portion and/or bottom portion of the housing can define recess(es) or openings configured to receive one or more retaining members extended from the pusher.

Although the delivery device 200 has been illustrated and described herein as including two sets of retaining members on the pusher 240 and three sets of recesses defined by the housing 210, in other embodiments, a delivery device can include any suitable number of retaining members and/or sets of retaining members (e.g., one, two, three, four or more retaining members and/or sets of retaining members), and any suitable number of recesses and/or sets of recesses (e.g., one, three, four or more recesses and/or sets of recesses). Further, in some embodiments, the retaining members can extend from one, two, three or four surfaces of the pusher. Still further, in some embodiments, a pusher of a delivery device can include a non-equal number of retaining members per surface or side of the pusher, and a housing of the delivery device can include recesses and/or openings corresponding to any suitable configuration of retaining members.

Each of the top portion 230 and the bottom portion 232 of the housing 210 is configured to be gripped or otherwise held by an operator during actuation of the delivery device 200. In some embodiments, each of the top portion 230 and bottom portion 232 can have a protrusion 270, 272, respectively, that extends from the elongate housing 210. For example, as shown in FIG. 3, the top and bottom portions 230, 232 have protrusions 270, 272, respectively, that extend in opposing directions from the elongate housing. The protrusions 270, 272 are sufficiently rigid such that they are configured to be gripped by or otherwise have the fingers of an operator of the delivery device 200 rested thereupon during actuation of the delivery device. In this manner, the dosage delivery device 200 is configured to facilitate single-handed actuation of the device by an operator. The protrusions 270, 272 can be substantially perpendicular to an outer surface of the respective top and bottom portions 230, 232 of the housing 210. As shown, when the pusher 240 is moved in the distal direction with respect to the housing 210, the elongate protrusion 248 of the pusher 240 is configured to contact the protrusion 270 on the top portion of the housing to limit further movement of the pusher in the distal direction with respect to the housing. Similarly stated, engagement of the elongate protrusion 248 of the pusher 240 with a face or other portion of the protrusion 270 of the top portion 230 of the housing 210 causes movement of the pusher in the distal direction to cease.

In some embodiments, at least one of the top portion 230 or the bottom portion 232 of the housing includes a textured outer surface portion 276. For example, as shown, each of the top portion 230 and bottom portion 232 of the housing 210 includes a textured surface portion 276, 276' that can include at least one of a plurality of ridges and/or a plurality of recesses (e.g., elongate parallel ridges and/or recesses). The textured surface portions 276, 276' can be configured to facilitate gripping of the delivery device 200 by an operator during actuation of the device.

In some embodiments, the delivery device 200 is individually packaged in a container (not shown), for example, until an operator is ready to operate the delivery device to deliver the dosage form therefrom. The container can be, for example, a sealed wrapper, a foil pouch, or the like. The container can also include an oxygen absorber or scrubber therein. A label can be applied to an outer surface of the container with written and/or pictorial instructions for operation of the delivery device 200. In some embodiments, as described in more detail herein, the delivery device 200 can be individually packaged in the container such that the pusher 240 is separate or detached from the housing 210.

In use, a container including the delivery device 200 is optionally opened and the delivery device is removed therefrom. Optionally, the operator inspects the delivery device to ensure that it is unused, such as looking to see whether the locking member is coupled to the pusher, the bridge (or breakable member) is unbroken or not at least partially separated from the housing, the distal end portion of the housing is deformed, whether a distal end portion of the push rod is extended from an opening at the distal end portion of the housing and/or whether the dosage form is disposed in the housing, as described herein. Once the operator determines that the delivery device is unused, or otherwise does not appear to have been tampered with, the operator continues with the operation of the delivery device. If the delivery device is suspected of being used and/or tampered with, the device can be discarded and a second delivery device can be obtained. In an embodiment in which the pusher was separated from, or otherwise not at least partially received within the actuation pathway of, the housing in the container, the operator can insert at least a portion of the pusher into the actuation pathway of the housing.

Optionally, a locking member is removed from the pusher of the delivery device, thereby permitting the device to be actuated. For example, the first and second side portions of a locking member are moved towards each other (e.g., squeezed together) to remove flange portions of the locking member from being disposed about portions of the pusher, and then the locking member is separated or moved away from the pusher. Optionally, the locking member can be discarded.

The delivery device 200 is positioned with respect to a mouth of a subject (which may or may not be the operator of the device) for delivery of the dosage form to the subject's oral mucosa. The operator optionally places first and second fingers (e.g., the index and middle fingers) on the protrusions (e.g., on at least a portion of a distal facing surface of each protrusion) extended from each of the top and bottom portions of the housing, and another finger (e.g., the thumb) on the end cap of the pusher. The operator then applies an actuation force to the pusher (e.g., via the thumb) to move the pusher from its first position towards its second position. A force exerted by the pusher on the bridge of the housing at least partially breaks the bridge. Optionally, the pusher also pushes the bridge into a recess defined by the housing adjacent the channel.

A distal end portion of the pusher contacts a distal end portion of the housing, causing the housing to deform and produce an opening through which the dosage form can be expelled. A contoured surface of the distal end portion of the pusher contacts the dosage form, and moves the dosage form in a distal direction with respect to the housing to expel the dosage form through the opening produced in the housing to the subject's oral mucosa. Optionally, the delivery device is discarded after delivery of the dosage form therefrom.

In some embodiments, as shown in FIGS. 3 and 6, the housing 210 defines an aperture 278 in communication with the actuation pathway 212. The aperture 278 can be disposed, for example, proximate to the protrusion 270 of the top portion 230 of the housing 210. The aperture 278 can be in communication with the channel 212 defined by the housing 210. For example, the aperture 278 can be formed by the housing 210 at a distal end of the channel 221. The aperture 278 can be sized to permit passage of the dosage form 20 therethrough.

During manufacturing, the aperture 278 can be used to pass the dosage form 20 into the actuation pathway for loading the dosage form into the delivery device. The pusher 240 can be inserted into the actuation pathway 212 via an opening 223 at the proximal end portion 216 of the housing 210. The distal end portion 242 of the pusher 240 picks up the dosage form within the actuation pathway 212 adjacent the aperture 278, and moves the dosage form to the volume at the distal end portion 214 of the housing. Once the pusher 240 is inserted into the actuation pathway, the retaining members prevent the pusher from being retracted.

The embodiments described herein can be used with any suitable drug dosage form (or drug-containing tablet), for example, those including sufentanil compositions. Such sufentanil compositions can include any of the compositions described in U.S. Pat. No. 8,753,308, entitled "Methods for Administering Small Volume Oral Transmucosal Dosage Forms Using a Dispensing Device," which is incorporated herein by reference in its entirety. In other embodiments, however, the devices and methods described herein can be used to deliver any other drug composition.

The embodiments described herein can have any suitable dimensions for delivery of a dosage form to a subject, and more specifically for oral transmucosal delivery of a dosage form to a subject. For example, in some embodiments, the delivery device can include a housing (e.g., housing 210) that is about 5 cm to about 10 cm in length, about 6 cm to about 8 cm in length, or about 6.5 cm in length. The delivery device can include a pusher (e.g., pusher 240) that is about 5 cm to about 10 cm in length, about 7 cm to about 9 cm in length, or about 7.5 cm in length. In some embodiments, the pusher has a greater length than the housing. The pusher can have a height (or thickness) of about 0.05 cm to about 0.1 cm, about 0.07 cm to about 0.09 cm, or about 0.8 cm. In some embodiments, the cantilevered portion (e.g., cantilevered portion 228) of the housing (e.g., housing 210) can have any suitable length, including, but not limited to, a length of about 0.25 cm to about 2.5 cm, and more particularly a length within the range of about 0.6 cm to about 0.8 cm. For example, in some embodiments, the housing 210 has a length of about 6.5 cm, and the cantilevered portion 228 has a length of about 0.7 cm.

The embodiments described herein can be formed or constructed of one or m ore biocompatible materials. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes, and/or blends and copolymers thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof.

Further, in some embodiments, at least a portion of the delivery devices described herein can be constructed of a transparent material. For example, in some embodiments, at least a portion of the housing (e.g., housing 110, 210) is transparent. In this manner, the presence of the dosage form (e.g., dosage form 10, 20) in the volume can be visually confirmed through the housing prior to actuating the device. Also in this manner, the position of the push rod can be visually confirmed through at least a portion of the housing. In some embodiments, the housing may be constructed of a non-transparent, or opaque, material, but the housing may include a window, e.g., adjacent the volume to permit visual confirmation of whether a dosage form is contained within the volume. In some embodiments, a delivery device described herein can be configured to provide a different form of indicium (e.g., auditory, tactile) indicative of the dosage form being disposed therein. For example, a delivery device be configured to emit an auditory signal (e.g., a beep, chime, word or set of words, or the like) when the delivery device detects (e.g., via a sensor or the like) the presence of the dosage form therein. In another example, the delivery device can be configured to emit, an optionally amplify, an auditory signal caused by a movement of the dosage form from within the delivery device.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any embodiment described herein.

For example, although the dosage delivery device 100, 150 is shown and described herein as having a pusher 140, 190 with a retaining member 146, 196 and a housing 110, 160 with a recess 118, 168, in other embodiments, the dosage delivery device 100, 150 can include a set of retaining members and/or a set of recesses (or openings) as described with respect to dosage delivery device 200.

In another example, although the pusher 240 is shown as including a contoured distal end surface, in other embodiments, the pusher 240 can include a squared, tapered, or convex distal end surface, or have a differently shaped distal end surface suitable to deliver the dosage form from the delivery device.

In another example, although the pusher 140, 190, 240 is shown and described herein as being coupled to the housing 110, 160, 210 such that at least a portion of the pusher 140, 190, 240 is disposed within the actuation pathway 112, 162, 212 of the housing, in some embodiments, the pusher can have a first configuration in which the pusher is detached or separate from the housing, and a second configuration in which the pusher is at least partially disposed within the housing. In this manner, for example, the pusher can be configured to be inserted into the housing by a user or an operator of the delivery device at or near the time of intended administration of the drug dosage form using the delivery device. Such separation of the pusher from the housing containing the drug dosage form can help to prevent inadvertent actuation of the delivery device. In such an embodiment, for example, to prepare the delivery device 200 for administration of the dosage form 20, the distal end portion 242 of the pusher 240 is inserted into the opening 223 at the proximal end portion 216 of the housing 210. The distal end portion 242 can be advanced, or moved distally, within the actuation pathway until the pusher is in a desired position with respect to the housing 210 and/or the drug dosage form 20. For example, the distal end portion 242 of the pusher can be advanced within the actuation pathway 212 until the pusher is in the first position, as described herein. At least one retaining member 246, 246', 247, 247' of the pusher 240 can be sufficiently flexible or compressible with respect to the elongate body portion 249 of the pusher to permit such insertion of the pusher into the actuation pathway 212. In other words, one or more retaining members 246, 246', 247, 247' can be configured to move or otherwise compress towards or against the elongate body portion 249 of the pusher when the portion of the pusher including the retaining member is inserted into the actuation pathway of the housing 210 such that the retaining member does not interfere with insertion of the pusher 240 into the housing 210. In some embodiments, after the pusher is inserted into the housing of the delivery device such that the pusher is moved to the first position, the pusher cannot be removed from the housing, for example, due to engagement of at least one retaining member (e.g., retaining member 146, 246, 246', 247, 247') of the pusher with at least one recess (e.g., recess 118, 260, 262, 264) of the housing as described herein.

In another example, although the pusher has been shown and described herein as including at least one retaining member (e.g., retaining member 146, 246, 246', 247, 247') configured to be at least partially received in at least one recess or opening (e.g., recess 118, 260, 262, 264) of the housing, in other embodiments, the housing can include at least one retaining member and the pusher can define at least one recess or opening configured to receive the at least one retaining member of the housing. The retaining member(s) of the housing can be similar in many respects to any retaining member described herein, and the recess or opening of the pusher can be similar in many respects to any recess or opening of the portion of the housing defining the actuation pathway described herein.

In still another example, although the dosage delivery device 200 shown and described herein as including a first or top portion 230 with a deformable distal end portion 236, in some embodiments, the second or bottom portion 232 of the housing 210 includes a deformable distal end portion 234. The deformable distal end portion 234 of the second portion 232 can be similar in many respects, or identical, the deformable distal end portion 236 of the first portion 230 of the housing 210 described herein. In some embodiments, the distal end portion 236, 234 of both the first portion 230 and second portion 232, respectively, of the housing are deformable upon actuation of the delivery device 200. The degree or angle of deformation of each of the distal end portions 234, 236, can be the same or different. For example, the degree of deformation of the distal end portion 236 of the first portion 230 of the housing 210 can be greater than, less than, or equal to the degree of deformation of the distal end portion 234 of the second portion 232 of the housing, when the delivery device is in its second configuration.

Although the devices and methods are shown and described herein as providing for delivery of a single drug dosage form via a device configured for only a single actuation, in other embodiments, the devices and methods described herein can be applicable for delivery of multiple drug dosage forms, for example, during a single actuation of the device.

Although the devices, systems and methods are shown and described herein as providing for delivery of drug dosage forms to the oral mucosa, in other embodiments, the devices, systems and the methods described herein can be applicable for delivery of any suitable therapeutic substance to any portion of the anatomy.

Although the devices, systems and methods are shown and described herein as providing for delivery of a single drug dosage form, in other embodiments, any of the push-rods, housing or other components can be used in conjunction with a multi-dose delivery device, such as those described in U.S. Pat. No. 8,548,623, entitled "Storage and Dispensing Devices for Administration of Oral Transmucosal Dosage Forms," which is incorporated herein by reference in its entirety.

In some embodiments, the pusher and/or housing designs described herein can be used in either an actual drug delivery device or a simulated drug delivery device. A simulated drug delivery device can, for example, correspond to an actual drug delivery device and can be used, for example, to train a user in the operation of the corresponding actual medicament delivery device. Such simulated device can be devoid of actual drug-containing dosage forms. For example, such a simulated device can include a placebo dosage form, a plastic tablet (or tablet of any suitable material) having a similar geometry as a drug dosage form, or the like.

Similarly, where methods and/or events described above indicate certain events and/or procedures occurring in certain order, the ordering of certain events and/or procedures may be modified. While the embodiments have been particularly shown and described, it will be understood that various changes in form and details may be made.

What is claimed is:

1. An apparatus, comprising:
a housing defining an actuation pathway; and
a pusher, at least a portion of the pusher disposed within the actuation pathway such that a distal end portion of the pusher and a distal end portion of the housing define a volume configured to contain a drug-containing tablet, the pusher configured to move relative to the housing in a distal direction from a first position to a second position to expel the drug-containing tablet from the volume,
the actuation pathway being closed at the distal end portion of the housing when the pusher is in the first position, the pusher contacts a deformable portion of the distal end portion of the housing during movement of the pusher from the first position to the second position to deform the deformable portion of the distal end portion of the housing and produce an opening at the distal end portion of the housing such that the actuation pathway is open at the distal end portion of the housing when the pusher is in the second position, the housing including a cantilevered portion at least partially disposed within the deformable portion when the pusher is in the first position, the cantilevered portion configured to limit lift or rotation of the drug-containing tablet with respect to the housing when the drug-containing tablet is expelled from the volume, the deformable portion configured to deform away from the cantilevered portion when the pusher is moved in the distal direction relative to the housing to produce the opening.

2. The apparatus of claim 1, wherein the pusher includes an elongate body portion, the elongate body portion of the pusher includes a plurality of retaining members extended from a first side of the elongate body portion, the plurality of retaining members being disposed within the housing when the pusher is in the first position and when the pusher is in the second position, the plurality of retaining members being biased in a direction away from the elongate body portion of the pusher, the plurality of retaining members configured to engage or be at least partially received in a recess or opening defined by a sidewall of the housing defining the actuation pathway such that the plurality of retaining members and the housing collectively prevent movement of the pusher relative to the housing in a proximal direction.

3. The apparatus of claim 1, wherein:
the pusher includes a retaining member, the retaining member configured to inhibit movement of the pusher in a proximal direction with respect to the housing when the pusher is in the first position, the retaining member configured to inhibit movement of the pusher in the proximal direction with respect to the housing when the pusher is in the second position.

4. The apparatus of claim 1, wherein:
the pusher includes a plurality of retaining members,
the housing defines a first recess in communication with the actuation pathway, the housing defines a second recess in communication with the actuation pathway, the housing defines a third recess in communication with the actuation pathway, the second recess being distal to the first recess, the third recess being distal to the second recess, at least a portion of a first retaining member from the plurality of retaining members of the pusher being received in the first recess of the housing when the pusher is in the first position, at least a portion of the first retaining member being received in the second recess of the housing when the pusher is in the second position, at least a portion of a second retaining member from the plurality of retaining members of the pusher being received in the second recess of the housing when the pusher is in the first position, at least a portion of the second retaining member being received in the third recess of the housing when the pusher is in the second position,
the plurality of retaining members of the pusher configured to limit movement of the pusher in a proximal direction with respect to the housing when the first retaining member is received in the second recess and when the second retaining member is received in the third recess so that the pusher cannot be returned to the first position after the pusher is moved to the second position.

5. The apparatus of claim 1, wherein the housing includes a first portion and a second portion, a distal end portion of the first portion of the housing and a distal end portion of the second portion of the housing collectively defining the opening when the opening is produced, the distal end portion of the first portion of the housing including the deformable portion, the distal end portion of the second portion of the housing being undeformed when the opening is produced.

6. The apparatus of claim 5, wherein the deformable portion includes a curved inner surface extended across the actuation pathway, the curved inner surface of the deformable portion positioned over the actuation pathway when the opening is produced to limit a height of the actuation pathway so that at least one of the rotation or the lift of the drug-containing tablet with respect to the housing is limited when the drug-containing tablet is expelled.

7. The apparatus of claim 1, wherein the cantilevered portion is defined by an aperture of the housing, at least a portion of the deformable portion is distal to the aperture with respect to the housing.

8. The apparatus of claim 7, wherein an outer surface of the cantilevered portion of the housing is co-planar with an outer surface of the deformable portion adjacent to the cantilevered portion before the deformable portion is deformed, the cantilevered portion is exposed when the opening is produced.

9. The apparatus of claim 1, wherein the housing defines a channel and includes a bridge disposed within the channel, the bridge configured to engage an elongate protrusion of the pusher slidably disposed within the channel, the bridge configured to be at least partially separated from the housing when the pusher is moved from the first position to the second position, the housing defining a recess configured to receive at least a portion of the bridge when the bridge is at least partially separated from the housing.

10. The apparatus of claim 1, further comprising:
the drug-containing tablet, the drug-containing tablet being disposed in the volume when the pusher is in the first position, the drug-containing tablet including a dosage of sufentanil.

11. An apparatus, comprising:
a housing having a first portion and a second portion and defining an actuation pathway between the first portion and the second portion, a distal end portion of the first portion of the housing including a deformable portion configured to deform away from a distal end portion of the second portion of the housing to produce an opening for delivery of a drug-containing tablet from the housing, the deformable portion including an inner surface extended from a first side of the deformable portion of the housing to a second side of the deformable portion of the housing across the actuation pathway, the inner surface of the deformable portion being contoured to extend into the actuation pathway to limit a height of the actuation pathway to less than a diameter of the drug-containing tablet when the deformable portion is deformed so that the inner surface of the deformable portion limits at least one of rotation or lift of the drug-containing tablet with respect to the housing when the drug-containing tablet is expelled,
the housing including a cantilevered portion at least partially disposed within the deformable portion when the deformable portion is in an undeformed position, the cantilevered portion configured to limit at least one of the rotation or the lift of the drug-containing tablet with respect to the housing when the drug-containing tablet is expelled; and
a pusher, at least a portion of the pusher disposed within the actuation pathway and moveable in a distal direction with respect to the housing, the pusher contacts the distal end portion of the first portion of the housing during movement of the pusher in the distal direction to deform the deformable portion away from the cantilevered portion and away from the distal end portion of the second portion of the housing to produce the opening.

12. The apparatus of claim 11, wherein the housing has a first configuration in which the distal end portion of the first portion of the housing is in contact with the distal end portion of the second portion of the housing such that a distal end portion of the actuation pathway is closed and a second configuration in which the distal end portion of the first portion of the housing is spaced apart from the distal end portion of the second portion of the housing, the distal end portion of the second portion of the housing is undeformed in the second configuration.

13. The apparatus of claim 11, wherein a portion of the pusher is fixedly and irreversibly disposed between the distal end portion of the first portion of the housing and the distal end portion of the second portion of the housing after delivery of the drug containing tablet from the housing.

14. The apparatus of claim 11, wherein the housing includes an elongate housing body and a protrusion extended from the elongate housing body, a portion of the pusher configured to engage the protrusion of the housing when the pusher is moved in the distal direction with respect to the housing to inhibit further movement of the pusher in the distal direction with respect to the housing.

15. The apparatus of claim 11, wherein:
the distal end portion of the first portion of the housing includes non-deformable portions disposed on opposite sides of the actuation pathway, and
the deformable portion of the distal end portion of the first portion of the housing is disposed between the non-deformable portions of the distal end portion of the first portion of the housing.

16. The apparatus of claim 11, wherein the inner surface of the deformable portion includes a convex inner surface geometry extended across the actuation pathway.

17. The apparatus of claim 11, wherein the housing defines a channel and includes a bridge disposed within the channel, the bridge configured to engage an elongate protrusion of the pusher slidably disposed within the channel, the bridge configured to be at least partially separated from the housing when the pusher is moved in the distal direction with respect to the housing, the housing defining a recess configured to receive at least a portion of the bridge when the bridge is at least partially separated from the housing.

18. The apparatus of claim 11, wherein the pusher includes an elongate body portion and a plurality of retaining members extended from a first side of the elongate body portion, the plurality of retaining members configured to limit movement of the pusher in a proximal direction with respect to the housing.

19. The apparatus of claim 11, wherein:
the pusher includes a plurality of retaining members,
the housing defines a first recess in communication with the actuation pathway, the housing defines a second recess in communication with the actuation pathway, the housing defines a third recess in communication with the actuation pathway, the second recess being distal to the first recess, the third recess being distal to the second recess, at least a portion of a first retaining member from the plurality of retaining members of the pusher being received in the first recess of the housing when the pusher is in a first position, at least a portion the first retaining member being received in the second recess of the housing when the pusher is in a second position, at least a portion of a second retaining member from the plurality of retaining members of the pusher being received in the second recess of the housing when the pusher is in the first position, at least a portion of the second retaining member being received in the third recess of the housing when the pusher is in the second position,
the plurality of retaining members of the pusher configured to limit movement of the pusher in a proximal direction with respect to the housing when the first retaining member is received in the second recess and when the second retaining member is received in the third recess so that the pusher cannot be returned to the first position after the pusher is moved to the second position.

20. The apparatus of claim 11, further comprising:
the drug-containing tablet, the drug-containing tablet being disposed in a volume collectively defined by a distal end portion of the pusher, the distal end portion of the first portion of the housing, and the distal end portion of the second portion of the housing, the drug-containing tablet including a dosage of sufentanil.

* * * * *